United States Patent [19]

Sakakibara et al.

[11] Patent Number: 4,472,381
[45] Date of Patent: Sep. 18, 1984

[54] AMINO ACID DERIVATIVES, METHODS OF PREPARING SAID DERIVATIVES AND ANTIHYPERTENSIVE DRUGS CONTAINING THEM

[75] Inventors: Shumpei Sakakibara, Suita; Yasumi Yugari, Kamakura; Shigebumi Hashimoto, Yokohama, all of Japan

[73] Assignee: Ajinomoto Company Incorporated, Tokyo, Japan

[21] Appl. No.: 458,844

[22] Filed: Jan. 18, 1983

[30] Foreign Application Priority Data

Jan. 23, 1982 [JP] Japan .................................. 57-9341
Aug. 16, 1982 [JP] Japan .................................. 57-141831

[51] Int. Cl.³ ...................... A61K 37/00; C07C 103/52
[52] U.S. Cl. ............................. 424/177; 260/112.5 R
[58] Field of Search .................. 424/177; 260/112.5 R

[56] References Cited

PUBLICATIONS

Kenner, et al., Tetrahedron Letter No. 4, pp. 3623–3626, (1976).
Chung, et al., Tetrahedron, vol. 27, pp. 1205–1210, (1971).
Nishino, et al., Biochemistry, vol. 18, No. 20, (1979), 4340–4347.

*Primary Examiner*—Delbert R. Phillips
*Attorney, Agent, or Firm*—Oblon, Fisher, Spivak, McClelland & Maier

[57] ABSTRACT

The present invention relates to an amino acid derivative represented by the formula

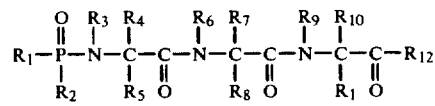

wherein $R_1$ and $R_2$ represent hydroxyl, alkyloxy, aryloxy, arylkyloxy, alkyl, aryl, or aralkyl; $R_3$, $R_5$, $R_8$ and $R_{11}$ are hydrogen or alkyl; $R_4$, $R_7$ and $R_{10}$ are hydrogen, or substituted or unsubstituted alkyl, aryl or aralkyl; $R_6$ and $R_9$ are hydrogen, alkyl, aryl, or aralkyl; $R_{12}$ is hydroxyl, alkyloxy, aryloxy, aralkyloxy, amino, mono- or di-alkyl-, aryl- or aralkyl amino; and $R_6$ and $R_7$ combined together, and $R_9$ and $R_{10}$ combined together independently may form a substituted or unsubstituted alkylene bridge. The present invention also relates to a method of preparing said amino acid derivatives, and to anti-hypertensive drugs containing them.

14 Claims, No Drawings

AMINO ACID DERIVATIVES, METHODS OF PREPARING SAID DERIVATIVES AND ANTIHYPERTENSIVE DRUGS CONTAINING THEM

BACKGROUND OF THE INVENTION

1. Field of the Invention

The present invention relates to novel amino acid derivatives and antihypertensive drugs containing them. The present invention also relates to methods of preparing these derivatives.

2. Detailed Description of the Invention

The present inventors have succeeded in the synthesis of novel amino acid derivatives represented by the general formula:

$$R_1-\underset{\underset{R_2}{|}}{\overset{\overset{O}{\|}}{P}}-N-\underset{\underset{R_5}{|}}{\overset{\overset{R_3}{|}}{C}}-\underset{\underset{O}{\|}}{\overset{\overset{R_4}{|}}{C}}-N-\underset{\underset{R_8}{|}}{\overset{\overset{R_6}{|}}{C}}-\underset{\underset{O}{\|}}{\overset{\overset{R_7}{|}}{C}}-N-\underset{\underset{R_1}{|}}{\overset{\overset{R_9}{|}}{C}}-\underset{\underset{O}{\|}}{\overset{\overset{R_{10}}{|}}{C}}-R_{12}$$

Moreover, the present inventors have found that these derivatives, having an antihypertensive activity, are useful as antihypertensive drugs and intermediates for their production, and, based on this finding, have completed the present invention.

$R_1$ and $R_2$ in the foregoing formula, being the same or different from each other, each individually represents hydroxyl, alkyloxy, aryloxy, aralkyloxy, alkyl, aryl, or aralkyl.

The alkyloxy is a lower alkyloxy having 1~5 carbon atoms such as methoxy, ethoxy, n-propyloxy, n-butyloxy, and n-pentyloxy.

The aryloxy is the one having 6~12 carbon atoms such as phenoxy, naphthyloxy, and p-tolyloxy.

The aralkyloxy is the one having 6~12 carbon atoms such as benzyloxy, phenetyloxy, phenylpropyloxy, and hydroxybenzyloxy.

The alkyl is a lower alkyl having 1~5 carbon atoms such as methyl, ethyl, n-propyl, n-butyl and n-pentyl.

The aryl is the one having 6~12 carbon atoms such as phenyl and p-tolyl.

The aralkyl is the one having 6~12 carbon atoms such as benzyl, phenethyl, and phenylpropyl.

$R_3$, $R_5$, $R_8$, and $R_{11}$ at least two of which are the same or all of which are different from one another, each individually represents hydrogen atom, or alkyl: for example, the one having 1~5 carbon atoms such as methyl, ethyl, n-propyl, n-butyl, and n-pentyl. That is to say, all of $R_3$, $R_5$, $R_8$, and $R_{11}$ may each individually represent hydrogen atom or methyl, or $R_3$ and $R_5$ may each individually represent hydrogen atom, and $R_8$ and $R_{11}$ may individually represents methyl; all of them may be different from one another: for example, $R_3$ represents hydrogen atom, $R_5$ represents methyl, $R_8$ represents ethyl, and $R_{11}$ represents isopropyl.

$R_4$, $R_7$, and $R_{10}$ at least two of which are the same or all of which are different from one another, each individually represents hydrogen atom, or substituted or unsubstituted alkyl, aryl, or aralkyl.

The alkyl represents a lower alkyl having 1~5 carbon atoms such as methyl, ethyl, n-propyl, isopropyl, n-butyl, isobutyl, sec-butyl, and n-pentyl.

The aryl represents the one having 6~12 carbon atoms such as phenyl, p-tolyl, and naphthyl.

The aralkyl represents the one having 6~12 carbon atoms such as benzyl and naphthylmethyl.

Substituent groups in the foregoing substituted groups may include, for example, hydroxyl, carboxyl, carbamoyl, amino guanidino, imidazolyl, indolyl mercapto, and lower alkylthio.

$R_6$ and $R_9$, being the same or different from each other, each individually represents hydrogen, alkyl, aryl, or aralkyl. The alkyl, the aryl, and the aralkyl, being, for example, the foregoing ones, may further include alicylic compounds such as cyclopropyl, cyclopentyl, and cyclohexyl; and aromatic ring-condensed alicyclic compounds such as 2-indanyl and 1-indanyl.

$R_{12}$ represents hydroxyl, alkyloxy, aryloxy, aralkyloxy, amino, mono- or di-alkyl-, aryl-, or aralkylamino. The alkyloxy, the aryloxy, the aralkyloxy, the alkyl, the aryl, and the aralkyl may each individually include, for example, those cited above as examples of $R_1$ and $R_2$.

$R_6$ and $R_7$, combined together, may form an alkylene bridge having 2~4 carbon atoms, an alkylene bridge having 2~3 carbon atoms and 1 sulfur atom, an alkylene bridge having 3~4 carbon atoms which contains a double bond, or substituted ones of these bridges; $R_9$ and $R_{10}$, combined together, may form the same alkylene bridges.

Examples of substituents on the foregoing bridges include hydroxyl, lower alkoxy, lower alkyl, oxo(o=), amino, condensed allyl, a condensed aromatic ring, and a condensed alicyclic ring.

Structures formed by such alkylene bridges may be, for example, the following ones:

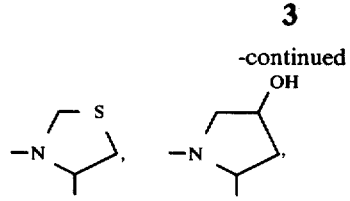

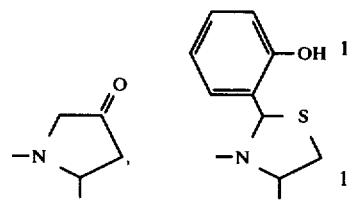

Amino acids constituting the amino acid derivatives of the present invention may be either the L-isomer or the D-isomer.

The amino acid derivatives of the present invention may be in the form of a salt, such as a metal salt, as for example, sodium, potassium, lithium, and calcium salts or a salt with an organic base. As the organic base, there can be adopted amines such as ammonia (ammonium salt), dicyclohexylamine, and N-methyl-D-glucamine; and basic amino acids such as lysine and arginine.

When the amino acid derivatives are to be included in the antihypertensive drugs of the present invention, they need to be in a form of a pharmaceutically acceptable salt.

The amino acid derivatives of the present invention are tripeptide derivatives of which the terminal amino group is combined with a phosphorus compound (P), being represented by the formula: P-X-Y-Z (X, Y, and Z each represents an amino acid residue).

The amino acid corresponding to X typically includes alanine, leucine, isoleucine, glycine, phenylalanine, arginine, glutamic acid, glutamin, lysine, valine, ornithine, methionine, serine, and threonine; the amino acid corresponding to Y typically includes proline, hydroproline, glycine, N-substituted glycine, and thioproline; the amino acid corresponding to Z typically includes proline, hydroxyproline, glycine, alanine, serine, aspartic acid, arginine, tyrosine, phenylalanine, valine, leucine, isoleucine, threonine, methionine, glutamic acid, glutamine, lysine, cystine, tryptophan, and histidine.

When the tripeptide derivative has functional groups, the functional groups may be protected by protecting groups ordinarily used in synthetic chemistry of peptides; the protected derivatives are also encompassed by the amino acid derivatives of the present invention.

Examples of methods for preparation are as follows:
Method 1:

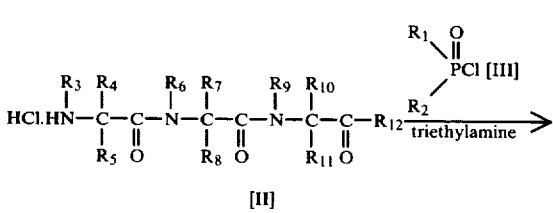

[II]

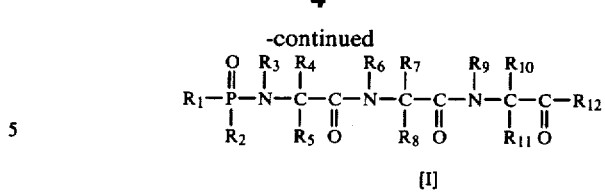

[I]

wherein $R_{1-12}$ each individually represents the same as defined above.

The desired compound can be prepared by causing a phosphoridate [III] such as phosphochloridatediester and phosphochloridatemonoester to react with, for example, a hydrochloride derivative of ester or amide of the tripeptide derivative [II] in an inert solvent such as methylene chloride in the presence of a base such as triethylamine to transform the N-terminal of an the tripeptide derivative into a phosphorus derivative, followed, if necessary, by selectively removing protecting groups by means of hydrolysis with an alkali, catalytic hydrogenation, or the like.

On the other hand, the desired compound can also be prepared by directly condensing a phosphoridate [III] with a free compound of the tripeptide derivative [II].

Method 2:

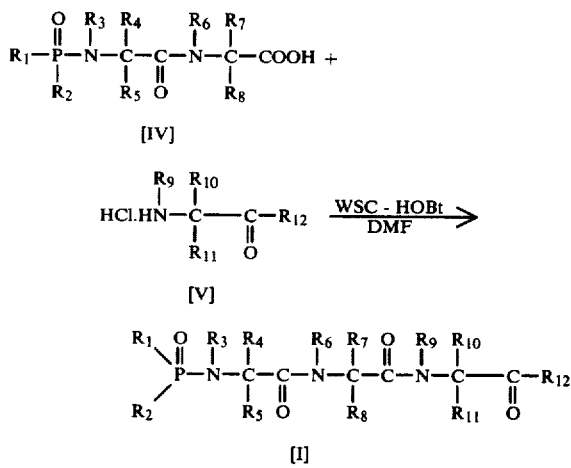

wherein $R_{1-12}$ each individually represents the same as defined above.

The desired compound can be prepared by subjecting a phosphorus derivative of a dipeptide [IV] and an amino acid derivative [V] such as a hydrochloride of ester or amide to a condensation reaction in an inert solvent such as dimethylformamide (DMF) with the use of a condensing agent such as N,N'-dimethylaminopropylethylcarbodiimide (WSC) and 1-hydroxybenzotriazole (HOBt) to obtain a phosphorus derivative of the tripeptide [I], followed, if necessary, by selectively removing protecting groups by means of hydrolysis with an alkali or catalytic hydrogenation.

Method 3:

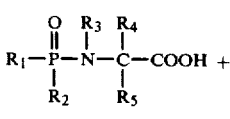

[VI]

-continued

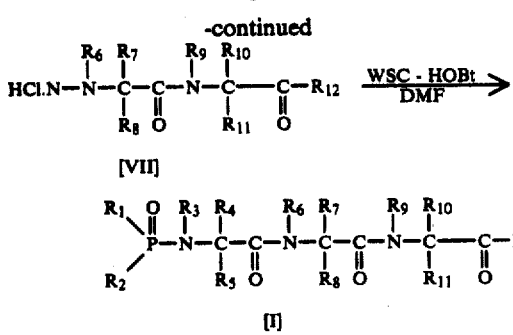

[VII]

[I]

wherein $R_{1\sim 12}$ each individually represents the same as defined above.

The desired compound can be obtained by subjecting a phosphorus derivative of an amino acid [VI] and a dipeptide derivative [VII] such as a hydrochloride of ester or amide to a condensation reaction in an inert solvent such as dimethylformamide with the use of a peptide condensating agent used in synthetic chemistry of peptides, such as WSC and HOBt, to obtain a phosphorus derivative of a tripeptide, followed, if necessary, by selectively removing protecting groups by means of hydrolysis with an alkali or catalytic hydrogenation.

The methods will be illustrated with more specific examples below.

A substituted phosphoryl derivative can be prepared by preparing a peptide derivative represented by the general formula:

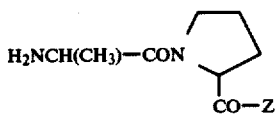

wherein Z represents the same as defined above, followed by causing the peptide derivative to react with a substituted phosphoryl halogenide such as diethyl- or dibenzylphosphoryl chloride. The substituted phosphoryl derivative, for example, dibenzylphosphoryl chloride, can be converted into a phosphoryl derivative by subjecting it to hydrogenation using palladium carbon as catalyst.

The foregoing tripeptide, an intermediate for the derivatives of the present invention, can be prepared by causing an alanine having a protected amino group to react with a proline having a protected carboxyl group to prepare alanylproline, removing the protecting groups of the alanylproline, and causing the resulting product to react with the Z component, an amino acid having a protected amino group, followed, if necessary, by removing the protecting group.

On the other hand, the tripeptide can also be prepared by preparing dibenzylphosphorylalanylproline, follwed by causing the product to react with the foregoing selected amino acid ester according to the method of Japanese patent first publication No. 104863/1981.

An alanylproline derivative of which the constituent proline residue has a hydroxyl group (hydroxyproline) can also be prepared in the same manner.

Those protecting groups for amino, imino, carboxyl, and hydroxyl groups, those methods for the protection, those methods for removal of the protecting groups, and those methods for amide-linking by condensation between amino and carboxyl groups which are all employed in the preparation of the derivatives of the present invention and intermediates therefore may be the ones ordinarily used in methods for peptide synthesis or generally or conventionally employed in the known literature, for example, Protein Chemistry, 1 Amino Acid.Peptide, e.g. pages 405~509 (1969), compiled by Shiro Akabori, Takeo Kaneko, and Kozo Narita, published by Kyoritsu Shuppan Co. An amide-linkage is advantageously formed from an amino acid by a condensation method in which an active ester of the amino acid having a protected amino group, such as p-nitrophenylester and N-hydroxysuccinimideester, is used for reaction. When a solvent is used in the reaction, DMF or water can be adopted as solvent. The reaction temperature may be a room temperature or so, but the reaction can also, as needed, be accelerated by heating.

The derivatives of the present invention are isolated from the reaction mixture by concentrating the reaction mixture to dryness, purifying the residue by means of column chromatography, followed by lyophilization of the product.

When the derivatives of the present invention are used, as an active ingredient, for an antihypertensive drug, there may be adopted their free forms, their non-toxic forms of salt, or their nontoxic forms having protecting groups. An amino acid constituting the derivatives for use as an antihypertensive drug of the present invention may be either the L-isomer or the D-isomer.

The amino acid derivatives of the present invention are useful as an antihypertensive drug for treating hypertensive mammals including humans. The derivatives can be used for lowering blood pressure by formulating them into a preparation such as tablets, capsules, and elixirs for oral administration and into an aspetic liquid preparation or an aseptic suspension preparation for parenteral administration. The amino acid derivatives of the present invention can be administered to a subject necessitating such treatment (animals and humans) in a dosage range of 0.2~500 mg per subject generally several times a day, that is, in a total daily dosage of 1~2000 mg. The dosage varies according to the seriousness of disease, the body weight of subjects, and other factors acknowledged by those skilled in the art.

The amino acid derivatives of the present invention can also be administered together with diuretics or other antihypertensive drugs. Typically, these drugs are administered in a dosage combination of which one unit of daily dose is in the range from ⅕ times as large as a clinical dosage minimally recommended, to a level maximally recommended singly for each entity of disease. These combinations are specially shown as follows: A kind of antihypertensive drugs of the present invention which is clinically effective in a daily dosage range of 15~200 mg can effectively be administered together with the following other antihypertensive drugs and diuretics in a daily dosage range of 3~200 mg: hydrochlorothiazide (15~200 mg), chlorothiazide (125~2000 mg), ethacrynic acid (15~200 mg), amiloride (5~20 mg), furosemide (5~80 mg), propranolol (20~480 mg), timolol (5~50 mg), methyldopa (65~2000 mg). The foregoing dosage ranges are adjusted on the basis of unit according to the necessity for the possible daily divided dosage. The dosage varies according to the seriousness of disease, the body weight of subject, and other factors acknowledged by those skilled in the art.

The foregoing typical combinations of drugs are formulated into pharmaceutical compositions stated below. About 0.2~500 mg of the derivatives of the present invention, pharmaceutically acceptable salt compounds, or mixtures of both are blended into unit dosage forms generally acknowledged or required for the pharmaceutical practice together with pharmaceutically acceptable vehicles, carriers, excipients, binders, antiseptics, stabilizers, flavorings, and so forth. The amount of each active substance in these compositions or preparations is adjusted in such a way as to give an appropriate dosage of the prescribed range.

Specific materials which can be incorporated into tablets, capsules, and so forth are as follows: A binder such as traganth, gum arabic, cornstarch, and gelatin; an excipient such as microcrystalline cellulose; a swelling agent such as cornstarch, pregelatinized starch, and arginic acid; a lubricant such as magnesium stearate; a sweetner such as sucrose, lactose, and saccharin; a flavoring such as peppermint, an oil from Gaultheria adenothrix Maxim, and cherry. When the unit dosage form of the preparation is a capsule, a liquid carrier such as fatty oil can further be incorporated in the foregoing type materials. Various other materials can be present as a coating material or in order to vary the physical form of unit dosage forms according to other methods. For example, tablets can be coated with shellac and/or sugar. Syrups or elixirs can contain active compounds, sucrose as a sweetner, methyl- and propylparaben as an antiseptic, a coloring matter, a flavoring such as cherry and an orange flavoring.

Aseptic compositions for injection can be formulated according to the usual practice for preparation of pharmaceutical dosage forms, in which practice an active substance is dissolved or suspended in a vehicle such as water for injection; natural vegetable oils such as sesame oil, palm oil, peanut oil, and cotton seed oil; and synthetic fat vehicle such as ethyl oleate. A buffer, an antiseptic, and an antioxidant can further be incorporated as occasion demands.

The present invention will be explained precisely in the following Examples.

Having now fully described the invention, it will be apparent to one of ordinary skill in the art that many changes and modifications can be made thereto without departing from the spirit or scope of the invention as set forth therein.

EXAMPLES

Example 1

Dibenzylphosphoryl-L-alanyl-L-prolyl-L-proline L-arginine salt:

A. Dibenzylphosphorylchloride

A phosphorus trichloride (3.7 g, 25 m mole) in benzene (15 ml) solution was added dropwise and slowly, to the mixture of dimethylaniline (6.1 g, 50 m mole) and benzylalcohol (5.4 g, 50 m mole) at a temperature of less than 15° C. by cooling with coolant of −15°· C. and stirring. After the addition, the mixture was further stirred for 30 minutes. To the mixture, benzylalcohol (2.7 g, 25 m mole) was further added dropwise and the mixture was reacted at a room temperature overnight.

The reaction solution was shaken with water (15 ml), and the thus obtained organic phase was separated and then washed with water, 5N aqueous ammonia and water in this order. The thus obtained mixture was dried over anhydrous sodium sulfate. The drying agent was removed by filtration and the remaining filtrate was distilled under reduced pressure leaving a non-coloured and oily dibenzylhalogen phosphite product (3.2 g).

The thus obtained oily material gave one spot by thin layer chromatography with silica gel (developing solvent; chloroform:ethanol:ethyl acetate=5:2:5, colour forming agent:Iodine).

Dibenzyl hyddrogen phosphite (6.7 g) was dissolved in carbon tetrachloride (70 ml) dried previously, and put in a 3-neck flask. Sulfurylchloride (3 g) in carbon tetrachloride (10 ml) solution was added dropwise to the above mixture at a temperature of less than 10° C. while cooling with coolant of −15° C. and stirring and at an atmosphere of nitrogen gas.

After the addition of sulfurylchloride, the mixture was stirred for 1.5 hours at room temperature at an atmosphere of nitrogen gas. It was confirmed that the starting material was completely consumed by tracing the reaction product by thin layer chromatography (developing solvent; chloroform:ethanol:ethyl acetate=5:2:5, colour forming agent:Iodine). Thus produced dibenzylphosphoryl chloride without further purification was used in the following reaction.

B. N-t-butyloxycarbonyl-L-alanyl-L-proline benzyl ester

N-t-butyloxycarbonyl-L-alanine (3.8 g, 20 m mole), L-proline benzyl ester hydrochloride (5 g, 20.6 m mole) and 1-hydroxy benzotriazole, which is hereinafter referred to as HOBt (2.7 g, 20 m mole) were suspended in tetrahydrofuran, which is hereinafter referred to as THF (50 ml). N,N'-dimethylaminopropylethylcarbodiimide, which is hereinafter referred to as WSC (3.8 ml) in THF (10 ml) solution was added dropwisely to the above suspended solution while cooling a −15° C. and stirring. The reaction was carried for 3 hours at a temperature of less than 0° C. and thereafter at room temperature overnight. The thus obtained solution was distilled under reduced pressure leaving a residue. The residue was dissolved in ethyl acetate and washed with 1N hydrochloric acid, water, 5% aqueous sodium bicarbonate and water in order, and dried over anhydrous sodium sulfate. The thus obtained solution was distilled under reduced pressure leaving a residue. The residue was recrystallized in ether-n-hexan to give N-t-butyloxycarbonyl-L-alanyl-L-proline benzyl ester (6.7 g, yield: 89%) having melting point of 71° to 72° C. This product gave one spot by thin layer chromatography (developing solvent; chloroform:methanol:acetic acid=95:5:3, colour forming method; spraying with 0.1% ninhydrin and heating).

C. N-t-butyloxycarbonyl-L-alanyl-L-proline

N-t-butyloxycarbonyl-L-alanyl-L-proline benzyl ester (6.4 g, 17 m mole) was dissolved in methanol (100 ml). Hydrogen was passed for 3 hours through the solution in the presence of 10% palladium-carbon as a catalyst. The catalyst was removed by filtration and the filtrate was distilled under reduced pressure leaving a residue. The residue was crystallized in ethyl acetate-n-hexan to give N-t-butyloxycarbonyl-L-alanyl-L-proline (4.5 g, yield: 92.4%) having melting point of 155° to 157° C. and specific rotatory power $[\alpha]_D^{25} = -90.5°$ (C=1, ethanol). The product gave a single spot on thin layer chromatography.

D. N-t-butyloxycarbonyl-L-alanyl-L-prolyl-L-proline benzyl ester

N-t-butyloxycarbonyl-L-alanyl-L-proline (4.3 g, 15 m mole), L-proline benzyl ester hydrochloride (3.7 g, 15.3 m mole) and HOBt (2.0 g, 15 m mole) were dissolved in methylene dichloride (40 ml). WSC (2.8 ml) was added dropwise to the above mixture while cooling to −15° C. and stirring. The reaction was carried out for 3 hours at a temperature of not more than 0° C., and then overnight at room temperature. The solvent was removed by distillation under reduced pressure leaving a residue. The residue was dissolved in ethyl acetate, and washed with 1N hydrochloric acid, water, 5% sodium bicarbonate and water, in order. The mixture was dried over anhydrous sodium sulfate. The solvent thus obtained solution was distilled under reduced pressure leaving a residue. The residue was crystallized with a mixture of ethyl acetate and n-hexan to give a crystal of N-t-butyloxycarbonyl-L-alanyl-L-prolyl-L-proline benzyl ester (6.3 g, 88.7%) having melting point of 143° to 145° C. and specific rotatory power of $[\alpha]_D^{25} = -131.0°$ (C=1, chloroform).

E. Dibenzylphosphoryl-L-alanyl-L-prolyl-L-proline benzyl ester

N-t-butyloxycarbonyl-L-alanyl-L-prolyl-L-proline benzyl ester (6.0 g, 12.7 m mole) was dissolved in 4.8N hydrogen chloride in dioxan (15 ml) under shaking and stirred for 40 minutes at room temperature. The solvent was distilled off under reduced pressure and dried ethyl ester was added thereto. Thus obtained precipitate was obtained on the paper filter and soon put into the desiccator containing sodium hydroxide to be dried. All amount of the precipitate was dissolved in DMF (30 ml) and cooled to a temperature of −5° C. Triethyl amine was added to the cold mixture to neutralize it. Dibenzylphosphoryl chloride in carbon tetrachloride solution synthesized in the same manner described above and triethyl amine were slowly and dropwise added to the above neutralized solution at not more than 5° C. while cooling and stirring. In such case, the PH value of the reaction solution was always maintained from 8 to 9. After the completion of the addition, the reaction was carried out at room temperature overnight. The thus obtained solution was distilled under reduced pressure leaving a residue. To thus obtained residue ethyl acetate (300 ml) was added and the mixture was washed with 1N hydrochloric acid, water, 5% sodium bicarbonate, and water in order and then dried with anhydrous sodium sulfate. The solution was distilled under reduced pressure leaving an oily dibenzylphosphoryl-L-alanyl-L-prolyl-L-proline benzyl ester material (7.7 g, 96%). The oily material gave a single spot with $R_f=0.65$ by the thin layer chromatography (developing solvent; chloroform:methanol:acetic acid=95:5:3, colour forming method; spraying of 25% hydrobromic acid and 0.1% ninhydrine and heating).

F. Dibenzylphosphoryl-L-alanyl-L-prolyl-L-proline L-arginine salt

The oily material obtained above was dissolved in a mixture (20 ml) of acetone and methanol (1:1), and 1N sodium hydroxide (15 ml) was added thereto under cooling with ice-bath. The mixture was stirred for 1.5 hours at room temperature and was neutralized with 1N hydrochloric acid. The organic solvent was distilled off under reduced pressure. The residue was dissolved in ethyl acetate and washed with 1N hydrochloric acid and water, and dried with anhydrous sodium sulfate. The solvent was distilled off under reduced pressure to give oily dibenzylphosphoryl-L-alanyl-L-prolyl-L-proline (5.7 g). The oily material gave a single spot with $R_f$ of 0.5 by the thin layer chromatography (developing solvent; chloroform:methanol:acetic acid=95:5:3, colour forming method; spraying of 25% hydrobromic acid and 0.1% ninhydrine, and heating).

The oily material (660 mg) was dissolved in ethanol (5 ml) and an aqueous L-arginine solution (1.2 ml) was added thereto. The arginine solution has been prepared by dissolving L-arginine in the water in a ratio of 1.74 g of L-argine in 10 ml of the solution.

The solvent was distilled off under reduced pressure, and then water was completely removed by azeotropic distillation with toluene. The residue was recrystalized from methanol and ethyl acetate yielding dibenzylphosphoryl-L-alanyl-L-prolyl-L-proline L-arginine salt crystals (620 mg) having a melting point 114° C. (s) to 122° C. (d) and specific rotatory power $[\alpha]_D^{20} = -73.3°$ (C=1.16, ethanol). A fixed weight of the sample of the product was heated in 6N hydrochloric acid at 110° C. for 17 hours, and from thus hydrolized material, amino acids analysis was carried out. The ratio of alanine, proline and arginine was 1.00:2.01:1.01.

Elementary analysis: Found C 50.65%, H 7.11%, N 12.30%; Calculation C 50.17%, H 7.16%, N 12.41% as $C_{33}H_{48}O_9N_7P.4H_2O$.

Median lethal dose (LD 50):
more than 15 g/kg in mouse
more than 15 g/kg in rat

Example 2

Dibenzylphosphoryl-L-alanyl-L-prolyl-L-serine L-arginine salt:

Dibenzylphosphoryl-L-alanyl-L-proline (1.2 g, 2.5 m mole) as shown in the Japanese patent first publication No. 104863/1981, HOBt (338 mg, 2.5 m mole) and L-serine methylester hydrochloride (467 mg, 3 m mole) were suspended in DMF (10 ml), and WSC (0.5 ml) was added dropwise thereto while cooling to −15° C. and stirring. The reaction was carried out for 3 hours under cooling and next overnight at a room temperature. Ethyl acetate (100 ml) was added to the reaction solution, washed 1N hydrochloric acid and water in order, and dried with anhydrous sodium sulfate. The thus obtained solution was distilled under reduced pressure to give an oily dibenzylphosphoryl-L-alanyl-L-prolyl-L-serine methyl ester (1.3 g). The oily product gave a single spot with $R_f 0.46$ by thin layer chromatography (developing solvent; chloroform:methanol:acetic acid=95:5:3, colour forming method: spraying of 25% hydrobromic acid and 0.1% ninhydrine and heating). The oily material was dissolved in a mixture (20 ml) of acetone and methanol (1:1) and 1N sodium hydroxide (5 ml) was added thereto under cooling with ice. The mixture was stirred for 1.5 hours at room temperature and neutralized with 1N hydrochloric acid. The solution was distilled under reduced pressure to eliminate the organic solvent, and the residue was dissolved in ethyl acetate, washed with 1N hydrochloric acid and water in order, and dried with anhydrous sodium sulfate. The thus obtained solution was distilled under reduced pressure to give oily dibenzylphosphoryl-L-alanyl-L-prolyl-L-serine (1.2 g). The oily material gave a single spot with $R_f 0.18$ by thin layer chromatography (developing solvent: chloroform:methanol:acetic acid=95:5:3, colour forming method; spraying of 25% hydrobromic acid and 0.1% ninhydrine, and heating).

The oily material (380 mg) was dissolved in ethanol (5 ml) and the aqueous L-arginine solution (0.71 ml) as prepared above. The solution was distilled under the reduced pressure leaving a residue, and residual water was removed completely by azeotropic distillation with toluene. To the residue, methanol was added and an insoluble material was separated by filtration. The filtrate was distilled under reduced pressure to give an amorphous powder of dibenzylphosphoryl-L-alanyl-L-prolyl-L-serine L-arginine salt (230 mg).

A fixed weight of the sample was heated in 6N hydrochloric acid at 110° C. for 19 hours. From this hydrolized product, amino acids analysis was carried out. The ratio of alanine, proline, serine and arginine was 1.00:1.02:0.96:1.07.

Example 3

Dibenzylphosphoryl-L-alanyl-L-prolyl-L-aspartic acid L-arginine salt:

Dibenzylphosphoryl-L-alanyl-L-proline (1.2 g, 2.5 m mole), HOBt (338 mg, 2.5 m mole) and L-aspartic acid dibenzylester P-toluene sulfonic acid salt (1.45 g, 3 m mole) were suspended in DMF (10 ml), and WSC (0.5 ml) was added dropwise thereto while cooling at −15° C. and stirring. The reaction was carried out under cooling for 3 hours and thereafter at room temperature overnight. To the reaction solution ethyl acetate (100 ml) was added and thus obtained mixture was washed with 1N hydrochloric acid and water in order, and dried with anhydrous sodium sulfate. The thus obtained solution was distilled under reduced pressure leaving a residue to obtain oily dibenzylphosphoryl-L-alanyl-L-prolyl-L-asparatic acid dibenzylester (1.9 g). The oily material gave a single spot with $R_f$ 0.75 by thin layer chromatography (developing solvent; chloroform:methanol:acetic acid = 95:5:3, colour forming method: spraying of 25% hydrobromic acid and 0.1% ninhydrine, and heating). This oily material was dissolved in a mixture (20 ml) of acetone and methanol (1:1), and 1N sodium hydroxide (5 ml) was added thereto while cooling. Next, the mixture was stirred for 1.5 hours at room temperature and neutralized with 1N hydrochloric acid. The organic solvent was removed by distillation under reduced pressure, and the residue was dissolved in ethyl acetate, washed with 1N hydrochloric acid and water and dried with anhydrous sodium sulfate. The solvent was removed by distillation under reduced pressure to obtain oily dibenzylphosphoryl-L-alanyl-L-prolyl-L-aspartic acid (1.6 g). The oily material gave a single spot with $R_f$ 0.15 by thin layer chromatography (developing solvent; chloroform:methanol:acetic acid = 95:5:3, colour forming method: spraying of 25% hydrobromic acid and 0.1% ninhydrine, and heating).

The oily material (430 mg) was dissolved in ethanol (5 ml), and aqueous arginine solution (0.76 ml), which has been prepared by dissolving L-arginine in water in the ratio of 1.74 g of L-arginine per 10 ml of the aqueous arginine solution, was added thereto. The solvent was removed by distillation under reduced pressure, and then the water was removed completely by azeotropic distillation with toluene. Methanol was added to the residue, and thus prepared insoluble material was separated by filtration. The solvent was distilled off under reduced pressure to obtain amorphous powder of dibenzylphosphoryl-L-alanyl-L-prolyl-L-aspartic acid L-arginine salt (390 mg).

The fixed weight of the sample was heated in 6N hydrochloric acid at 110° C. for 19 hours. For thus obtained hydrolized material, amino acids analysis was carried out. The ratio of alanine, proline, aspartic acid and arginine was 1.00:0.97:1.04:1.04.

Example 4

Dibenzylphosphoryl-L-alanyl-L-prolyl-L-tyrosine L-arginine salt:

Dibenzylphosphoryl-L-alanyl-L-proline (1.2 g, 2.5 m mole), HOBt (338 mg, 2.5 m mole) and L-tyrosine ethylester hydrochloride (737 mg, 3 m mole) was suspended in DMF (10 ml), and WSC (0.5 ml) was added gradually thereto while cooling to −15° C. and stirring. The reaction was carried out for 3 hours under cooling and then overnight at room temperature. To the reaction solution ethyl acetate (100 ml) was added, and the mixture was washed with 1N hydrochloric acid and water in order, and dried with anhydrous sodium sulfate. The solvent was removed by distillation under reduced pressure to obtain an oily dibenzylphosphoryl-L-alanyl-L-prolyl-L-tyrosine ethylester (1.4 g). This oily material gave a single spot with $R_f$ 0.50 by thin layer chromatography (developing solvent; chloroform:methanol:acetic acid = 95:5:3, colour forming method: spraying of 25% hydrobromic acid and 0.1% ninhydrine, and heating).

The oily material was dissolved in a mixture of acetone and methanol (1:1), and 1N sodium hydroxide (5 ml) was added thereto while cooling. Next, the mixture was stirred for 1.5 hours at room temperature, and neutralized with 1N hydrochloric acid. The thus obtained solution was distilled under reduced pressure leaving a residue and the residue was dissolved in ethyl acetate, washed with 1N hydrochloric acid and water and dried with anhydrous sodium sulfate. The thus dried solution was distilled under reduced pressure to obtain an oily dibenzylphosphoryl-L-alanyl-L-prolyl-L-tyrosine material (1.2 g). The oily material gave a single spot with $R_f$ 0.3 by thin layer chromatography (developing solvent; chloroform:methanol:acetic acid = 95:5:3, colour forming method: spraying of 25% hydrobromic acid and 0.1% ninhydrine, and heating).

The oily material (390 mg) was dissolved in ethanol (5 ml), and aqueous arginine solution (0.64 ml) prepared as above mentioned was added thereto. The thus obtained solution was distilled under reduced pressure leaving a residue and water was removed completely by azeotropic distillation with toluene. To the residue, methanol was added and the thus obtained insoluble material was removed by filtration, and the filtrate was distilled leaving an amorphous powder of dibenzylphosphoryl-L-alanyl-L-prolyl-L-tyrosine L-arginine salt (370 mg). A fixed weight of the sample (the product) was heated in 6N hydrochloric acid for 19 hours at 110° C., and amino acids in thus hydrolized material were analyzed. The ratio of alanine, proline, tyrosine and arginine was 1.00:0.99:1.03:1.02.

Example 5

Dibenzylphosphoryl-L-alanyl-L-prolyl-L-phenylalanyl L-arginine salt:

Dibenzylphosphoryl-L-alanyl-L-proline (1.2 g, 2.5 m mole), HOBt (338 mg, 2.5 m mole) and L-phenylalanine ethylester hydrochloride (690 mg, 3 m mole) were suspended in DMF (10 ml) and WSC (0.5 ml) were added thereto while cooling to −15° C. and stirring. The reaction was carried out for 3 hours under cooling and then overnight at room temperature. To the reaction solution, ethyl acetate (100 ml) was added, and the mixture was washed with 1N hydrochloric acid and water in order, and dried with anhydrous sodium sulfate. The the dried solution was distilled under reduced pressure to obtain an oily dibenzylphosphoryl-L-alanyl-L-prolyl-L-phenylalanine ethylester material (1.3 g). The oily material gave a single spot with $R_f$ 0.7 by thin layer chromatography (developing solvent; chloroform:methanol:acetic acid = 95:5:3, colour forming method:

spraying of 25% hydrobromic acid and 0.1% ninhydrine, and heating).

The oily material was dissolved in a mixture (20 ml) of acetone and methanol (1:1) and 1N sodium hydroxide (5 ml) was added under cooling. The mixture was stirred for 1.5 hours at room temperature, and neutralized with 1N hydrochloric acid. The thus neutralized solution was distilled under reduced pressure leaving a residue and the residue was dissolved in ethyl acetate, washed with 1N hydrochloric acid and water, and dried with anhydrous sodium sulfate. The thus dried solution was distilled under reduced pressure leaving an oily dibenzylphosphoryl-L-alanyl-L-prolyl-L-phenylalanine (0.9 g). The oily material gave a single spot with $R_f$ 0.42 by thin layer chromatography (developing solvent; chloroform:methanol:acetic acid=95:5:3, colour forming method: spraying of 25% hydrobromic acid and 0.1% ninhydrine, and heating).

The oily material (280 mg) was dissolved in ethanol (5 ml), and the aqueous arginine solution (0.47 ml) as previously described was added thereto. The hydrochloric solution was distilled under reduced pressure leaving a residue and water was completely removed by azeotropic distillation with toluene. To the residue, methanol was added and the thus prepared insoluble matter was separated by filtration. The filtrate was distilled under reduced pressure leaving a dibenzylphosphoryl-L-alanyl-L-prolyl-L-phenylalanine L-arginine salt material (270 mg). The fixed weight of the sample was heated in 6N hydrochloric acid for 19 hours at 110° C. In the thus hydrolized material amino acids were analyzed. The ratio of alanine, proline, phenylalanine and arginine was 1.00:1.00:1.08:1.05.

Example 6

Dibenzylphosphoryl-L-alanyl-L-prolyl-glycine L-arginine salt:

Dibenzylphosphoryl-L-alanyl-L-proline (1.2 g, 2.5 m mole), HOBt (338 mg, 2.5 m mole) and glycine benzylester p-toluene sulfonic acid salt (1.0 g, 3 m mole) were suspended in DMF (10 ml), and WSC (0.5 ml) was dropwise added thereto while cooling to −15° C. and stirring. The reaction was carried out for 3 hours under cooling, and next, overnight at room temperature. To the reaction solution ethyl acetate (100 ml) was added and the mixture was washed with 1N hydrochloric acid and water in order, and dried with anhydrous sodium sulfate. The thus dried solution was distilled under reduced pressure to give an oily dibenzylphosphoryl-L-alanyl-L-prolyl-glycine benzylester material (1.5 g). The oily material gave a single spot with $R_f$ 0.7 by thin layer chromatography (developing solvent; chloroform:methanol:acetic acid=95:5:3, colour forming method: spraying of 25% hydrobromic acid and 0.1% ninhydrine and heating).

This oily material was dissolved in a mixture (20 ml) of acetone and methanol (1:1) and 1N sodium hydroxide (5 ml) was added thereto under cooling. Next, the mixture was stirred for 1.5 hours at room temperature, and neutralized with 1N hydrochloric acid. The thus neutralized solution was distilled under reduced pressure leaving a residue, and the residue was dissolved in ethyl acetate, washed with 1N hydrochloric acid and water in order, and dried with anhydrous sodium sulfate. The thus dried solution was distilled under reduced pressure leaving an oily dibenzylphosphoryl-L-alanyl-L-prolylglycine material (1.4 g). The oily material gave a single spot with $R_f$ 0.4 by thin layer chromatography (developing solvent; chloroform:methanol:acetic acid=95:5:3, colour forming method: spraying of 25% hydrobromic acid and 0.1% ninhydrine and heating).

The oily material (610 mg) was dissolved in ethanol (5 ml) and the aqueous arginine solution as previously described (1.2 ml) was added thereto. The hydrochloric solution was distilled under reduced pressure, and further water was removed completely by azeotropic distillation with toluene leaving a residue. To the residue methanol was added and the insoluble material was separated by filtration. The thus obtained filtrate was distilled under reduced pressure to obtain an amorphous powder of dibenzylphosphoryl-L-alanyl-L-prolyl-glycine L-arginine salt material (570 mg). The fixed weight of the sample was heated in 6N hydrochloric acid for 19 hours at 110° C. In the hydrolized material, amino acids were analyzed. The ratio of alanine, proline, glycine and arginine was 1.00:0.91:1.00:1.11.

Example 7

Dibenzylphosphoryl-L-alanyl-L-prolyl-L-valine L-arginine salt:

By using L-valine benzylester hydrochloride (15.3 m mole) in place of L-proline benzylester hydrochloride (3.7 g, 15.3 m mole) as used in Example 1, the same experiment as in Example 1 is repeated and thereby dibenzylphosphoryl-L-alanyl-L-prolyl-L-valine L-arginine salt can be produced.

Example 8

Phosphoryl-L-alanyl-L-prolyl-L-proline L-arginine salt:

Dibenzylphosphoryl-L-alanyl-L-prolyl-L-proline L-arginine salt (3 g, 4.2 m mole), and L-arginine (1.45 g, 8.36 m mole) were dissolved in a mixture of ethanol (50 ml) and water (10 ml), and palladium-carbon (1 g) was added thereto. After that catalytic reduction reaction was carried out for 5 hours. The catalyst was removed by filtration and the solvent was removed by distillation. The residue was dissolved in water and freeze-dried to obtain phosphoryl-L-alanyl-L-prolyl-L-proline tri-L-arginine salt (3.63 g). After hydrolysis of the material with 6N hydrochloric acid, amino acids were analyzed. The ratio of alanine, proline and arginine was 1.00:1.99:2.90.

Example 9

Dibenzylphosphoryl-L-alanyl-L-prolyl-L-leucine L-arginine salt:

By using L-leucine benzylester hydrochloride (15.3 m mole) in place of L-proline benzylester hydrochloride (3.7 g, 15.3 m mole) as used in Example 1, the same experiment as in Example 1 is repeated, and thereby dibenzylphosphoryl-L-alanyl-L-prolyl-L-leucine L-arginine salt can be produced.

Example 10

Dibenzylphosphoryl-L-alanyl-L-prolyl-L-threonine,- L-methionine or -L-glutamic acid L-arginine salt:

By using hydroxyl group-protected-L-threonine, L-methionine or L-glutamic acid benzylester hydrochloride (15.3 m mole) in place of L-proline benzylester hydrochloride (3.7 g, 15.3 m mole) as used in Example 1, the same experiments as in Example 1 are repeated and the protective group is removed, if necessary, and thereby the titled objective amino acid derivatives can be produced.

Example 11

Dibenzylphosphoryl-L-alanyl-L-prolyl-L-proline amide:

Dibenzylphosphoryl-L-alanyl-L-proline (2.8 g, 6.4 m mole), HOBt (952 mg, 7 m mole), and L-proline amide (805 mg, 7 m mole) were dissolved in DMF (10 ml), and N,N'-dimethylaminopropylethylcarbodiimide hydrochloride (1.34 g, 7 m mole) was added thereto while cooling to −15° C.

The reaction was continued for 3 hours under cooling and then overnight at room temperature, the DMF solution was distilled under reduced pressure, and the residue was dissolved in chloroform. The mixture was washed with water, dried with anhydrous sodium sulfate, and the solvent was removed by distillation.

The residue was reprecipitated from methanol-ethyl ether to obtain dibenzylphosphoryl-L-alanyl-L-prolyl-L-prolineamide (890 mg). Melting point: 89° C. The specific rotatory power $[\alpha]_D^{20} = -29.9°$ (C=0.4, 1N acetic acid). After hydrolysis of the product with 6N hydrochloric acid, the amino acids were analyzed. The ratio of alanine, proline and ammonia was 1.00:0.99:1.05.

Example 12

Dibenzylphosphoryl-L-alanyl-L-prolyl-L-alanine L-arginine salt:

Dibenzylphosphoryl-L-alanyl-L-proline (1.4 g, 3.2 m mole), 1-hydroxybenzotriazol (476 mg, 3.5 m mole) and L-alanine benzylester p-toluene sulfonate (1.3 g, 3.5 m mole) were dissolved in DMF (5 ml), and WSC (0.64 ml) was added thereto while cooling to −15° C. The reaction was continued for 3 hours under cooling and then overnight at room temperature, and ethyl acetate (100 ml) was added thereto. The mixture was washed with 1N hydrochloric acid, 5% sodium bicarbonate and water in order, and dried with anhydrous sodium sulfate. The thus obtained solution was distilled under reduced pressure leaving an oily dibenzylphosphoryl-L-alanyl-L-prolyl-L-alanine benzylester material.

Thus obtained oily material was dissolved in acetone (25 ml), and 1N sodium hydroxide (4 ml) was added thereto while cooling with ice. Next, the mixture was stirred for 1 hour at room temperature and neutralized with 1N hydrochloric acid. The thus neutralized solution was distilled under reduced pressure, and the residue was dissolved in ethyl acetate. The mixture was washed with 1N hydrochloric acid and water in order, and dried anhydrous sodium sulfate. The solution was distilled under reduced pressure, and the thus obtained oily material was dissolved in ethanol (3 ml). The aqueous arginine solution (1.2 ml) as described above, was added thereto, and the aqueous solution was distilled under reduced pressure. Further, water was removed completely by azeotropic distillation with toluene. To the residue, ethanol was added and insoluble material was separated by filtration. By adding ethyl acetate to the filtrate, an amorphous powder (500 mg) was obtained. Melting point was 110°~120° C.

Elementary analysis: Found C 52.11%, H 7.09%, N 13.69%; Calculation C 52.19%, H 6.81%, N 13.74% as $C_{31}H_{46}N_{11}O_9P.1.2H_2O$.

After hydrolysis of the product with 6N hydrochloric acid, amino acids were analyzed. The ratio of alanine, proline and arginine was 1.94:1.03:1.00.

Example 13

Dibenzylphosphoryl-L-alanyl-L-prolyl-L-arginine:

Dibenzylphosphoryl-L-alanyl-L-proline (1.8 g, 4 m mole), HOBt (540 mg), and L-arginine methylester 2 hydrochloric acid salt (2.62 g, 10 m mole) were dissolved in DMF (30 ml), and then triethylamine (2.8 ml, 20 m mole) and dicyclohexylcarbodiimide (1.03 g) were added thereto while cooling to −15° C. The reaction was carried out for 4 hours under cooling and then overnight at room temperature. Thus produced dicyclohexylurea was separated by filtration. The solvent was distilled off and 0.1N hydrochloric acid was added to the residue. The mixture was washed with ethyl ether and the aqueous layer was absorbed with ion exchanging resin "Dia ion HP-20" as produced by Mitsubishikaseikogyo Co., Inc. The resin was washed with water and the desired substances were eluted with 80% methanol (methanol:5% acetic acid=80:20). The eluants were concentrated and the thus obtained residue was dissolved in acetone (10 ml). 0.1N sodium hydroxide (5 ml) was added to the mixture under cooling and the mixture was stirred for 1 hour at room temperature. The mixture was neutralized with 1N hydrochloric acid and the thus neutralized solution was distilled under reduced pressure leaving a residue. The residue was dissolved in water and treated with ion exchanging resins "Dia ion HP-20" for adsorption of the desired substances. The resin was washed with water and the desired substances were eluted with 80% methanol, which is the same composition as above. The eluants were concentrated and the thus obtained residue was dissolved in ethanol. To the solution ethyl ether was added to give an amorphous powder of dibenzylphosphoryl-L-alanyl-L-prolyl-L-arginine (800 mg). The specific rotatory power was $[\alpha]_D^{20} = -36.5°$ (C=0.5, ethanol).

Elementary analysis: Found C 54.60%, H 6.81%, N 13.54%; Calculation C 54.66%, H 6.62%, N 13.66% as $C_{28}H_{39}N_6O_7P.0.7H_2O$.

After hydrolysis of the product with 6N hydrochloric acid, amino acids were analyzed. Alanine:Proline:Arginine=1.00:1.01:1.00.

Example 14

Dibenzylphosphoryl-L-alanyl-L-prolyl-D-alanine L-arginine salt:

Dibenzylphosphoryl-L-alanyl-L-proline (1.4 g, 3.2 m mole), HOBt (476 mg, 3.5 m mole) and D-alanine benzylester p-toluene sulfonic acid salt (1.3 g, 3.5 m mole) were dissolved in DMF (5 ml), and WSC (0.64 ml) was added thereto while cooling to −15° C. The reaction was carried out for 3 hours under cooling and then overnight at room temperature. To the reaction solution ethyl acetate (100 ml) was added and the mixture was washed with 1N hydrochloric acid, 5% sodium bicarbonate and water in order. The mixture was dried with anhydrous sodium sulfate and the thus obtained solution was distilled under reduced pressure to give an oily dibenzylphosphoryl-L-alanyl-L-prolyl-D-alanine benzylester material.

The thus obtained oily material was dissolved in acetone (25 ml) and 1N sodium hydroxide (4 ml) was added under cooling. Next, the mixture was stirred for 1 hour at room temperature, and then neutralized with 1N hydrochloric acid. The solvent was removed by distillation under reduced pressure and the residue was dissolved in ethyl acetate. The mixture was washed with 1N hydrochloric acid and water, and dried with anhydrous sodium sulfate. The solution was distilled and the residue was dissolved in ethyl ether and n-hexan was added thereto to precipitate a crystal. The crystal was dissolved in ethanol and the aqueous arginine solution as mentioned above (1.2 ml) was added. The aqueous solution was distilled under reduced pressure and further, water was completely removed by azeotropic distillation with toluene. To the residue, ethanol was added, and a thus produced insoluble material was separated by filtration. To the filtrate, ethyl ether was added to precipitate dibenzylphosphoryl-L-alanyl-L-prolyl-D-alanine L-arginine salt (1.3 g) crystals. Melting point: 82°~85° C., Specific rotatory power $[\alpha]_D^{20} = -31.1°$ (C=0.5, ethanol).

Elementary analysis: Found C 51.70%, H 6.93%, N 13.79%; Calculation C 51.80%, H 6.87%, N 13.64% as $C_{31}H_{46}N_7O_9P \cdot 1.5H_2O$.

After hydrolysis of the product with 6N hydrochloric acid, amino acids were analyzed. Alanine:Proline:Arginine = 2.00:1.03:0.97.

Example 15

Dibenzylphosphoryl-L-alanyl-L-prolyl-D-proline L-arginine salt:

Dibenzylphosphoryl-L-alanyl-L-proline (1.4 g, 3.2 m mole), HOBt (476 mg, 3.5 m mole) and oily D-proline benzylester hydrochloride (968 mg, 4 m mole) were dissolved in DMF (5 ml) and WSC (0.64 ml, 3.5 m mole) were added thereto while cooling to −15° C. The reaction was carried out for 3 hours under cooling and then overnight at room temperature, and ethyl acetate (100 ml) was added to the reaction solution. The mixture was washed with 1N hydrochloric acid, 5% sodium bicarbonate and water in order, and then dried with anhydrous sodium sulfate. The solution was distilled under reduced pressure leaving an oily dibenzylphosphoryl-L-alanyl-L-prolyl-D-proline benzylester material.

The thus obtained oily material was dissolved in acetone (20 ml), and 1N sodium hydroxide (4 ml) was added thereto under cooling. The mixture was stirred for 2 hours at room temperature, and neutralized with 1N hydrochloric acid. The thus neutralized solution was distilled under reduced pressure, and the residue was dissolved in ethyl acetate. The mixture was washed with 1N hydrochloric acid and water in order, and then dried with anhydrous sodium sulfate. The solution was distilled under reduced pressure, the residue was dissolved in ethanol (3 ml), and the aqueous arginine solution as mentioned above (1.2 ml) was added thereto. The thus obtained aqueous solution was distilled under reduced pressure, and further, water was completely removed by azeotropic distillation with toluene. To the residue, ethanol was added and insoluble material was separated by filtration. By adding ethyl ether to the filtrate, an amorphous powder of dibenzylphosphoryl-L-alanyl-L-prolyl-D-proline L-arginine salt (585 mg) was obtained.

Elementary Analysis: Found C 50.43%, H 7.09%, N 12.39%; Calculation C 50.17%, H 7.16%, N 12.41% as $C_{33}H_{48}N_7O_9P \cdot 4H_2O$.

After hydrolysis of the product with 6N hydrochloric acid, amino acids were analyzed.
Alanine:Proline:Arginine = 1.00:2.08:1.01

Example 16

Dibenzylphosphoryl-L-alanyl-L-prolyl-trans-L-hydroxyproline L-arginine salt:

Dibenzylphosphoryl-L-alanyl-L-proline (1.4 g, 3.2 m mole), HOBt (476 mg, 3.5 m mole), and trans-L-hydroxyproline benzylester p-toluene sulfonic acid salt (1.4 g, 3.5 m mole) were dissolved in DMF, and WSC (0.64 ml, 3.5 m mole) was added thereto while cooling to −15° C. The reaction was carried out for 3 hours under cooling and then overnight at room temperature. To the reaction solution ethyl acetate (100 ml) was added and the mixture was washed with 1N hydrochloric acid, 5% sodium bicarbonate and water in order, and dried with anhydrous sodium sulfate. The thus obtained solution was distilled under reduced pressure leaving an oily dibenzylphosphoryl-L-alanyl-L-prolyl-trans-L-hydroxyproline benzylester material.

Thus obtained oily material was dissolved in acetone (15 ml), and 1N sodium hydroxide (4 ml) was added thereto under cooling with ice. The mixture was stirred for 2 hours at room temperature and neutralized with 1N hydrochloric acid.

The solvent was distilled off under reduced pressure and the residue was dissolved in water, and washed with ethyl acetate. The water solution was treated with ion exchanging resin "Dia ion HP-20" for adsorption of desired product. The resin was washed with water and the desired product was eluated with 80% methanol (methanol:5% acetic acid = 80:20). The eluate was concentrated under reduced pressure and the residue was dissolved in ethanol, and the aqueous arginine solution as mentioned above (1.2 ml) was added thereto. The thus obtained aqueous solution was distilled under reduced pressure and further water was completely removed by azeotropic distillation with toluene. To the residue, ethanol was added and an insoluble material was separated by filtration. Ethyl ether was added to the filtrate to obtain an amorphous powder of dibenzylphosphoryl-L-alanyl-L-prolyl-trans-L-hydroxyproline L-arginine salt (450 mg). After hydrolysis of the product with 6N hydrochloric acid, amino acids were analyzed. Alanine:Proline:Hydroxyproline:Arginine = 1.00:1.04:0.98:0.78.

Example 17

Dibenzylphosphoryl-L-alanyl-trans-L-hydroxyprolyl-L-proline:

A. t-butyloxycarbonyl-L-alanyl-trans-L-hydroxyproline t-Butyloxycarbonyl-L-alanine (2.84 g, 1.5 m mole) and trans-L-hydroxyproline benzylester p-toluene sulfonic acid salt (5.91 g, 15 m mole) were dissolved in methylene dichloride (50 ml) and WSC (2.75 ml, 15 m mole) was added thereto while cooling to −15° C. The reaction was carried out for 2 hours under cooling and then for 3 hours at room temperature, and the methylene dichloride solution was distilled under reduced pressure leaving a residue. The residue was dissolved in ethyl acetate (100 ml) and washed with 1N hydrochloric acid, 5% sodium bicarbonate and water in order, and dried with anhydrous sodium sulfate. The solvent was distilled off under reduced pressure to obtain oily t-butyloxycarbonyl-L-alanyl-trans-L-hydroxyproline benzylester.

The thus obtained oily material was dissolved in methanol (100 ml), and palladium-carbon (500 mg) was added thereto. The reductive reaction was carried out for 5 hours. The catalyst was removed by filtration and the solvent was distilled off under reduced pressure. The residue was recrystalized with ethyl acetate-hexan to give t-butyloxycarbonyl-L-alanyl-trans-L-hydroxyproline (3.7 g).

B. t-butyloxycarbonyl-L-alanyl-trans-L-hydroxyprolyl-L-proline benzylester t-Butyloxycarbonyl-L-alanyl-trans-L-hydroxyproline (3.02 g, 10 m mole) and L-proline benzylester hydrochloride (2.66 g, 11 m mole) were dissolved in methylene dichloride (50 ml) and WSC (2.01 ml, 11 m mole) was added thereto while cooling to −15° C. The reaction was carried out for 3 hours at room temperature. The methylene dichloride solution was distilled under reduced pressure and the residue was dissolved in ethyl acetate (100 ml), and washed with 1N hydrochloric acid, 5% sodium bicarbonate and water in order, and dried with anhydrous sodium sulfate. The thus obtained solution was distilled under reduced pressure and the residue was recrystalized with ethyl acetate-n-hexan to obtain t-butyloxycarbonyl-L-alanyl-trans-L-hydroxyprolyl-L-proline benzylester (4.1 g).

C. Dibenzylphosphoryl-L-alanyl-L-trans-L-hydroxyprolyl-L-proline t-Butyloxycarbonyl-L-alanyl-L-trans-L-hydroxyprolyl-L-proline benzylester (2.93 g, 6 m mole) and trifluoroacetic acid (10 ml) were mixed, and stirred for 40 minutes. Trifluoroacetic acid was distilled off under reduced pressure, and 4.8N hydrochloric acid dioxane solution (1.88 ml, 9 m mole) was added to the residue. The mixture was stirred well and ethyl ether was added thereto.

Thus produced precipitate was obtained on the filter paper and dried over sodium hydroxide in the desiccator. The precipitate was dissolved in DMF (3 ml) and neutralized by adding triethylamine (1.4 ml) while cooling to −5° C. Dibenzylphosphorylchloride carbon tetrachloride solution (10 m mole) and triethylamine were added thereto at not more than 5° C. and at pH 8 to 9. The mixture was stirred for three hours and distilled under reduced pressure until a residue was obtained. The residue was dissolved in ethyl acetate (100 ml) and washed with 1N hydrochloric acid, 5% sodium bicarbonate and water in order, and dried with anhydrous sodium sulfate. The solvent was removed by distillation under reduced pressure to obtain dibenzylphosphoryl-L-alanyl-trans-L-hydroxyprolyl-L-proline benzylester.

Thus obtained oily material was dissolved in methanol (20 ml) and 1N sodium hydroxide (6 ml) was added thereto while cooling with ice, and stirred for 3 hours at room temperature. The mixture was neutralized with 1N hydrochloric acid, and the solvent was distilled off under reduced pressure. The residue was dissolved in water and treated with ion exchanging resin "Dia ion HP-20" for adsorption of the desired product. The resin was washed with water, and the desired product was eluted with 80% methanol. The eluate was concentrated and the residue was recrystalized with ethyl acetate-n-hexan to obtain dibenzylphosphoryl-L-alanyl-trans-L-hydroxyprolyl-L-proline (650 mg). After hydrolysis of the product with 6N hydrochloric acid, amino acids were analyzed. Alanine:Proline:Hydroxyproline = 1.00:0.99:0.99.

Example 18

Dibenzylphosphoryl-L-isoleucyl-L-prolyl-L-proline L-arginine salt:

The oily t-Butyloxycarbonyl-L-isoleucyl-L-prolyl-L-proline benzylester (10 g, 20 m mole) and trifluoroacetic acid (50 ml) were mixed together under cooling, and stirred for 50 minutes. The trifluoroacetic acid solution was distilled under reduced pressure, and the residue was dissolved in DMF (50 ml). The mixture was neutralized with triethylamine (3.5 ml) under cooling to −5° C., and thereafter dibenzylphosphorylchloride carbontetrachloride solution (30 m mole) and triethylamine were dropwise added thereto at not more than 5° C. and at the pH range 8-9. The mixture was stirred for 3 hours at room temperature and then distilled under reduced pressure. The residue was dissolved in ethyl acetate (300 ml) and washed with 1N hydrochloric acid, 5% sodium bicarbonate and water in this order, and dried with anhydrous sodium sulfate. The thus obtained solution was distilled under reduced pressure to obtain an oily dibenzylphosphoryl-L-isoleucyl-L-prolyl-L-proline benzylester.

All the amounts of the oily material was dissolved in acetone (100 ml) and 1N sodium hydroxide (25 ml) was added thereto under cooling with ice and the mixture was stirred for 2 hours at room temperature. The mixture was neutralized with 1N hydrochloric acid, and distilled under reduced pressure to obtain a residue. The residue was dissolved in ethyl acetate. The mixture was washed with 1N hydrochloric acid and water in this order, dried with anhydrous sodium sulfate and distilled under reduced pressure until a residue was obtained. The residue was dissolved in ethanol, and the solution prepared by dissolving L-arginine (1.3 g) in water (3 ml) was added, and the resulting insoluble material was separated by filtration. The filtrate was distilled under reduced pressure leaving a residue.

The residue was recrystalized with ethanol-ethyl acetate to obtain dibenzylphosphoryl-L-isoleucyl-L-prolyl-L-proline L-arginine salt (4.3 g). Melting point: 141° to 148° C. A specific rotatory power: $[\alpha]_D^{20} = -84.9°$ (C=0.5, 50% ethanol).

Elementary analysis: Found C 53.28%, H 7.20%, N 12.65%; Calculation C 53.11%, H 7.44%, N 12.05% as $C_{36}H_{54}O_9N_7P \cdot 3H_2O$.

After hydrolysis of the product with 6N hydrochloric acid, amino acids were analyzed. Isoleucine:Proline:Arginine = 1.03:2.00:0.99

Example 19

Dibenzylphosphoryl-glycyl-L-prolyl-L-proline L-arginine salt:

Trifluoroacetic acid (10 ml) was added to t-butyloxycarbonylglycyl-L-prolyl-L-proline (1.85 g, 5 m mole) while cooling and the mixture was stirred for 40 minutes. The trifluoroacetic acid solution was distilled under reduced pressure, and to the residue, ethyl ether was added. The thus produced precipitate was obtained on the filter paper, and dissolved in DMF (10 ml). The mixture was neutralized by adding triethylamine (1.5 ml) to the mixture while cooling to −5° C., and dibenzylphosphorylchloride carbon tetrachloride solution (7 m mole) and triethylamine were dropwise added thereto while keeping a temperature not more than 5° C., and keeping a pH range to 8-9. The mixture was stirred for 3 hours at room temperature and distilled until a residue was obtained. The thus obtained residue was dissolved in ethyl acetate (100 ml), washed with 1N hydrochloric acid and water in this order, and dried with anhydrous sodium sulfate. The solution was distilled and the residue was dissolved in ethanol, and L-arginine (690 mg) water (2 ml) solution was added thereto. Water was removed by distillation of the solvent and by azeotropic distillation with toluene. To the residue, ethanol was added and an insoluble material was separated by filtration. Ethyl ether was added to the filtrate to obtain dibenzylphosphorylglycyl-L-prolyl-L-proline L-arginine salt (430 mg).

After the hydrolysis of the product, amino acids were analyzed, Glycine:Proline:Arginine=1.00:1.96:0.96.

Example 20

Dibenzylphosphoryl-L-phenylalanyl-L-Prolyl-L-proline:

t-Butyloxycarbonyl-L-phenylalanyl-L-prolyl-L-proline benzylester (1.65 g, 3 m mole) and trifluoroacetic acid (10 ml) were mixed together for 40 minutes under cooling. The trifluoroacetic acid solution was distilled under reduced pressure, and the residue was dissolved in DMF (5 ml). The mixture was neutralized by adding triethylamine (0.8 ml) thereto while cooling to −5° C., and further dibenzylphosphorylchloride carbon tetrachloride solution (5 m mole) were added dropwise while keeping a temperature to not more than 5° C. The pH range of reaction solution was usually kept from 8 to 9 by adding triethylamine. The mixture was stirred for 3 hours at room temperature, and then distilled until a residue was obtained. The residue was dissolved in ethyl acetate (100 ml) and washed with 1N hydrochloric acid, 5% sodium bicarbonate and water in order, and dried with anhydrous sodium sulfate. The thus obtained solution was distilled under reduced pressure to obtain an oily dibenzylphosphoryl-L-phenylalanyl-L-prolyl-L-proline benzylester material. The oily material was dissolved in acetone (20 ml) and 1N sodium hydroxide (4 ml) was added thereto while cooling with ice and the mixture was stirred for 3 hours at room temperature. After neutralization of the mixture with 1N hydrochloric acid, the thus neutralized solution was distilled under reduced pressure. The residue was dissolved in ethyl acetate. The mixture was dried with 1N hydrochloric acid and water in order, and dried with anhydrous sodium sulfate. The thus obtained solution was distilled under reduced pressure, and the residue was reprecipitated with ethyl acetate and n-hexan to obtain dibenzylphosphoryl-L-phenylalanyl-L-prolyl-L-proline (820 mg).

After hydrolysis of the product with 6N hydrochloric acid, amino acids were analyzed. Phenylalanine:Proline=0.99:2.00.

Example 21

Dibenzylphosphoryl-L-arginyl-L-prolyl-L-proline

Anisole (0.5 ml) was added to amyloxycarbonyl-tosyl-L-arginyl-L-prolyl-L-proline benzylester (1.45 g, 2 m mole) and anhydrous hydrogen fluoride (20 ml) was added thereto while cooling to −40° C. The reaction was carried out for 60 minutes at 0° C., and anhydrous hydrogen fluoride solution was distilled under reduced pressure. The residue was washed with ethyl ether, and dissolved in 1N acetic acid. The mixture was passed through adsorbent "Dowex 1×2" (type of $CH_3COO^-$) as produced by Dow Chemical Co. and the desired product was eluated with water. The eluted was freeze-dried. Thus obtained amorphous L-arginyl-L-prolyl-L-proline was dissolved in DMF (8 ml) and water (2 ml), and triethylamine (0.3 ml) was added thereto while cooling to −5° C. for neutralization.

To the mixture dibenzylphosphorylchloride carbon tetrachloride solution (3 m mole) and triethylamine were added dropwise while keeping the temperature to not more than 5° C., and keeping usually pH value to 8–9. The mixture was stirred for 3 hours at room temperature, then distilled off under reduced pressure, and the residue was dissolved in water and then passed through "Dowex 1×2" (a type of $CH_3COO^-$). The desired product was eluted with water and the thus obtained eluate was freeze-dried. The thus obtained amorphous powder was further purified by column chromatography with silica gel (eluating solution; chloroform:methanol:acetic acid=85:15:5). Main ingredients were collected and freeze-dried to obtain amorphous powder of dibenzylphosphoryl-L-arginyl-L-prolyl-L-proline (270 mg).

After hydrolysis of the product with 6N hydrochloric acid, amino acids were analyzed. Arginine:Proline=1.04:2.00.

Example 22

Dibenzylphosphoryl-L-glutamyl-L-prolyl-L-proline

Anisole (0.5 ml) was added to t-butyloxycarbonyl-γ-benzyl-L-glutamyl-L-prolyl-L-proline (1.06 g, 2 m mole) and anhydrous hydrogen fluoride (20 ml) was added thereto while cooling −40° C. The reaction was carried out for 1 hour at 0° C., and then the anhydrous fluoride solution was distilled under reduced pressure. The residue was washed with ethyl ether and then dissolved in 1N acetic acid, and the mixture was passed through ion exchange resin "IR-45" ($CH_3COO^-$). The desired product was eluated with water and the eluted was freeze-dried.

The thus obtained amorphous L-glutamyl-L-propyl-L-proline was dissolved in DMF (8 ml) and water (2 ml), and neutralized by addition of triethylamine (0.2 ml) while cooling to −5° C. Dibenzylphosphorylchloride carbon tetrachloride solution (3 m mole) and triethylamine were added dropwise to the mixture while keeping the temperature to not more than 5° C. and usually keeping the pH value to 8–9. The mixture was stirred for 3 hours at room temperature, and the solution was distilled under reduced pressure leaving a residue. The residue was dissolved in 5% sodium bicarbonate and then washed with ethyl acetate. The aqueous phase was acidified with 1N hydrochloric acid, and the desired product was extracted with ethyl acetate. The ethyl acetate phase was washed with sodium chloride solution and dried with anhydrous sodium sulfate. The ethyl acetate was distilled off under reduced pressure. The residue was re-precipitated with ethyl acetate-ethyl ether to obtain dibenzylphosphoryl-L-glutamyl-L-prolyl-L-proline (140 mg).

After hydrolysis of the product with 6N hydrochloric acid, amino acids were analyzed. Glutamic acid:Proline=0.92:2.00.

Example 23

Diethylphosphoryl-L-lysyl-L-prolyl-L-proline L-arginine salt:

A. t-Butyloxycarbonyl-ε-carbobenzoxy-L-lysyl-L-proline benzylester t-Butyloxycarbonyl-ε-carbobenzoxy-L-lysine dicylohexylamine salt (10 g, 17.8 m mole) was suspended in ethyl acetate, and washed with 1N sulfuric acid. Ethyl acetate phase was washed with water and dried with anhydrous sodium sulfate, and ethyl acetate was distilled off under reduced pressure.

All the obtained oily t-butyloxycarbonyl-ε-carbobenzoxy-L-lysine and L-proline benzylester hydrochloride (4.3 g, 17.8 m mole) were dissolved in methylene dichloride and WSC (3.3 ml, 17.8 m mole) was added thereto while cooling to −15° C. The mixture was stirred overnight and the methylene dichloride solution was distilled under reduced pressure leaving a residue. The residue was dissolved in ethyl acetate. The ethyl acetate solution was washed with 1N hydrochloric acid, 5% sodium bicarbonate and water in order, and dried with anhydrous sodium sulfate. The ethyl acetate was distilled off under reduced pressure to obtain an oily t-butyloxycarbonyl-$\epsilon$-carbobenzoxy-L-lysyl-L-proline benzylester.

All the thus obtained oily material was dissolved in methanol (20 ml) and 1N sodium hydroxide (20 ml) was added thereto under cooling. The mixture was stirred for 3 hours, and the aqueous solution was adjusted to pH 7 by addition of 1N hydrochloric acid. The methanol was distilled off under reduced pressure. The aqueous solution was adjusted to pH 2 by addition of 1N hydrochloric acid, and the desired product was extracted with ethyl acetate. The ethyl acetate phase was washed with water and dried with anhydrous sodium sulfate. The ethyl acetate solution was distilled under reduced pressure leaving an oily t-butyloxycarbonyl-$\epsilon$-carbobenzoxy-L-lysyl-L-proline.

All the above oily material was dissolved in DMF (20 ml), and L-proline benzylester hydrochloride (4 g, 16.7 m mole), HOBt (2.2 g, 16.7 m mole) and WSC (3 ml, 16.7 m mole) were added thereto while cooling to $-15°$ C.

The mixture was stirred overnight and excess of ethyl acetate was added thereto. The ethyl acetate solution was washed with 1N hydrochloric acid, 5% sodium bicarbonate and water in order, and dried with anhydrous sodium sulfate. The ethyl acetate solution was distilled under reduced pressure leaving an oily t-butyloxycarbonyl-$\epsilon$-carbobenzoxy-L-lysyl-L-prolyl-L-proline benzylester residue (11 g).

B. Diethylphosphoryl-L-lysyl-L-prolyl-L-proline L-arginine salt

Trifluoroacetic acid (50 ml) was added to the oily t-butyloxycarbonyl-$\epsilon$-carbobenzoxy-L-lysyl-L-prolyl-L-proline benzylester (11 g) under cooling and the mixture was stirred for 40 minutes. Trifluoroacetic acid was distilled off under reduced pressure and the residue was dissolved in DMF (30 ml), and was neutralized by addition of triethylamine, and then diethylphosphorylchloride carbon tetrachloride solution (25 m mole) was added thereto while keeping the temperature to not more than 5° C. and keeping usually pH value to 8–9. The mixture was stirred for 4 hours at room temperature. The solvent was distilled off under reduced pressure and the residue was dissolved in ethyl acetate, and washed with 1N hydrochloric acid, 5% sodium bicarbonate and water in order. The solution was dried with anhydrous sodium sulfate, and the solvent was distilled off under reduced pressure to obtain an oily diethylphosphoryl-$\epsilon$-carbobenzoxy-L-lysyl-L-prolyl-L-proline benzylester (9.5 g). The oily material (9.5 g) was dissolved in methanol (100 ml) and palladium-carbon (5 g) was added thereto, and thereafter catalytic reductive reaction was carried out for 4 hours. The catalyst was removed by filtration and the solution was distilled under reduced pressure leaving an oily diethylphosphoryl-L-lysyl-L-prolyl-L-proline residue. The oily material was dissolved in ethanol and L-arginine (2.3 g) water (4 ml) solution was added thereto. The solvent was distilled off under reduced pressure and water was removed by azeotropic distillation with toluene. Ethanol was added to the residue, and the thus produced insoluble material was removed by filtration. By adding ethyl acetate to the filtrate, diethylphosphoryl-L-lysyl-L-prolyl-L-proline L-arginine salt (3.5 g) was obtained.

After hydrolysis of the product with 6N hydrochloric acid, the material was subjected to amino acid analysis. Lysine:Proline:Arginine=0.99:1.57:1.00.

Example 24

Dibenzylphosphoryl-L-alanyl-L-prolyl-L-proline L-lysine salt:

L-lysine (701 mg, 4.8 m mole) was added to the oily dibenzylphosphoryl-L-alanyl-L-prolyl-L-proline (2.72 g, 5 m mole), and water (40 ml) was added thereto to dissolve the solid substances, and the solution was freeze-dried to obtain an amorphous powder of dibenzylphosphoryl-L-alanyl-L-prolyl-L-proline L-lysine salt (3.4 g).

Elementary analysis: Found C 53.94%, H 7.50%, N 9.58%; Calculation C 53.94%, H 7.27%, N 9.53% as $C_{33}H_{48}N_5O_9P\cdot2.5H_2O$.

Example 25

Diethylphosphoryl-L-alanyl-L-prolyl-L-proline L-arginine salt:

A. Diethylphosphorylchloride

Phosphorous acid diethylester (7 g, 50 m mole) was dissolved in carbon tetrachloride solution (50 m mole, 70 ml), and to the solution sulfurylchloride (6.8 g) carbon tetrachloride solution (25 ml) was added dropwise under the temperature not more than 5° C. with passing of nitrogen gas. After the addition, the mixture was stirred for 1.5 hours with passing of nitrogen gas. The reaction was traced by thin layer chromatography (developing solvent, chloroform:ethanol:ethyl acetate=5:2:5; Colour former, Iodine). It was confirmed that the starting materials were did not remaind in the reaction solution, and thus produced diethylphosphorylchloride was used for next step reaction without further purification.

B. Diethylphosphoryl-L-alanyl-L-proline benzylester

Trifluoroacetic acid (50 ml) was added to t-butyloxycarbonyl-L-alanyl-L-proline benzylester (11.3 g, 30 m mole) under cooling and the mixture was stirred for 40 minutes. Trifluoroacetic acid was distilled off under reduced pressure and the residue was dissolved in DMF and neutralized by addition of triethylamine (8 ml) under cooling to $-5°$ C. Next, diethylphosphorylchroride carbon tetrachloride solution (40 m mole) was added dropwisely thereto while keeping the temperature to not more than 5° C., and keeping pH value to 8–9 and the mixture was stirred overnight at room temperature. The solution was distilled under reduced pressure leaving a residue, and the residue was dissolved in ethyl acetate. The solution was washed with 1N hydrochloric acid, 5% sodium bicarbonate and water in order, and dried with anhydrous sodium sulfate. The solution was distilled under reduced pressure leaving an oily diethylphosphoryl-L-alanyl-L-proline benzylester residue (9.2 g).

C. Diethylphosphoryl-L-alanyl-L-prolyl-L-proline L-arginine salt:

The oily diethylphosphoryl-L-alanyl-L-proline benzylester (8.5 g, 20.6 m mole) was dissolved in methanol and palladium-carbon (2 g) was added thereto. The reductive reaction was carried out for 3 hours. The catalyst was removed by filtration and the solvent was distilled off under reduced pressure to obtain an oily diethylphosphoryl-L-alanyl-L-proline.

All the thus obtained oily material and L-proline benzylester hydrochloride (5.3 g, 22 m mole) were dissolved in methylene dichloride (50 ml) and WSC (4 ml, 22 m mole) was added thereto while cooling to −15° C. The mixture was stirred for 3 hours under cooling and overnight at room temperature, and the solution was distilled under reduced pressure leaving a residue. The residue was dissolved in ethyl acetate, and washed with 1N hydrochloric acid, 5% sodium bicarbonate and water in this order, and dried with anhydrous sodium sulfate. The solvent was distilled off under reduced pressure to obtain an oily diethylphosphoryl-L-alanyl-L-prolyl-L-proline benzylester (9.7 g).

The thus obtained oily material was dissolved in methanol, and palladium-carbon (2 g) was added thereto. The reductive reaction was carried out for 3 hours. The catalyst was separated by filtration and the solvent was distilled off under reduced pressure leaving a residue. The residue was purified by silica gel chromatography (solvent, chloroform:methanol:acetic acid = 95:5:3) to obtain an oily diethylphosphoryl-L-alanyl-L-prolyl-L-proline (3.1 g). The oily material was dissolved in ethanol and L-arginine (1.3 g) water (2 ml) solution was added thereto. The solution was distilled under reduced pressure to remove the solvent and water was removed by azeotropic distillation with toluene. Ethanol was added to the residue and the thus obtained insoluble material was separated by filtration. By adding ethyl acetate to the filtrate, diethylphosphoryl-L-alanyl-L-prolyl-L-proline arginine salt (1.3 g) was obtained. Melting point: 98° to 102° C., Specific rotatory power $[\alpha]_D^{20} = -77.9°$ C. (C=0.65 ethanol).

After hydrolysis of the product with 6N hydrochloric acid, amino acids were analyzed. Alanine:Proline:Arginine = 1.00:2.04:0.80.

Example 26

N-(O-benzyl-P-phenethylphosphonyl)-L-alanyl-L-prolyl-L-proline benzylester.

A. L-alanyl-L-prolyl-L-proline benzylester hydrochloride N-t-butyloxycarbonyl-L-alanyl-L-prolyl-L-proline benzylester (6.0 g, 12.7 m mole) as produced in the same manner as in Example 1, was dissolved in 4.8N hydrogene chloride dioxane solution, and the mixture was stirred for 1 hour at room temperature. The solvent was distilled off under reduced pressure and ethyl ether was added to the residue to obtain L-alanyl-L-prolyl-L-proline benzylester hydrochloride in crystalline form (5.18 g, yield: 99.7%).

B. Dibenzylphenethylphosphonate

Dibenzyl hydrogene phosphite (12.3 g, 50 m mole) was dissolved in DMF (80 ml), and sodium hydride (60% in oil, 2.2 g) was added to the mixture at an atmosphere of nitrogen while cooling to −15° C. and stirring. The thus obtained mixture was stirred for 1.5 hours at the temperature not more than 0° C. Phenethyl bromide (9.25 g, 50 m mole) in DMF (10 ml) solution was added dropwise to the above solution at an atmosphere of nitrogen at the temperature not more than 0° C. The thus obtained mixture was further reacted overnight at room temperature. DMF solution was distilled under reduced pressure leaving a residue and the residue was dissolved in ethyl ether. The resulting solution was washed with water, and dried with anhydrous sodium sulfate. The solution was distilled under reduced pressure leaving an oily dibenzylproduct. The product was crystallized at room temperature and further recrystallized with ethyl ether to obtain dibenzylphenethylphosphonate (6.5 g, yield: 35.5%) having melting point: 48° to 49° C.

B. Monobenzylphenethylphosphochloridate

Dibenzylphenethylphosphonate (3.19 g, 8.7 m mole) was dissolved in carbon tetrachloride (5 ml) and phosphorus pentachloride (1.91 g, 9.2 m mole) was added thereto under cooling in the ice bath, and the mixture was stirred for 30 minutes. The mixture was heated to 70° C. in the rate of 10° C. per 15 minutes and stirred for 30 minutes at 70° C. The reaction was carried out to completion for 2 hours at 70° C./1 mmHg in the rotating evaporator, and then the solvent, phosphorus oxychloride and benzyl chloride were distilled off. It was confirmed that the starting materials were consumed thin layer chromatography on silica gel (developing solvent, benzene:ethyl acetate = 1.1, Confirmation of Spot: UV lamp). The thus produced monobenzylphosphochloridate was used for the following reaction without further purification.

C. N-(O-benzyl-P-phenethylphosphonyl)-L-alanyl-L-prolyl-L-proline benzylester

L-alanyl-L-prolyl-L-proline benzylester hydrochloride (2.5 g, 6.1 m mole) was dissolved in methylene dichloride (20 ml) and triethyl amine (1.85 g, 18.3 m mole) was added thereto. Monobenzylphenethylphosphochloridate which had been produced from dibenzylphenethylphosphonate (3.19 g, 8.7 m mole) was dissolved in methylene dichloride (10 ml). This solution was added dropwise to the above solution on an ice bath and the mixture was stirred overnight at room temperature. The reaction solution was washed with water and distilled under reduced pressure to eliminate the solvent. The residue was dissolved in ethyl acetate and the mixture was washed with 1N hydrochloric acid, water, 5% sodium bicarbonate and water in order, and dried with anhydrous sodium sulfate. The solution was distilled under reduced pressure leaving a sticky residue and it was purified by column chromatography (silica gel, developing solvent; ethyl acetate:methanol = 20:1) to obtain N-(O-benzyl-P-phenethylphosphonyl)-L-alanyl-L-proline benzylester (1.58 g, yield: 41.7%). The product gave a single spot with $R_f$=0.4 by thin layer chromatography (developing solvent; ethyl acetate:methanol = 20:1, colour forming method: spraying of 25% hydrobromic acid and 0.1% ninhydrine and then heating).

NMR spectrum [CDCl$_3$, internal standard: TMS] ppm: 1.30 (2xd, 3H), 1.70~2.37 (m, 10H), 2.70~3.10 (m, 2H), 3.30~3.90 (m, 4H), 4.00~4.35 (m, 1H), 4.45~4.75 (m, 2H), 4.90~5.33 (m, 4H), 7.20 (S, 5H), 7.33 (S, 10H).

Example 27

N-(O-benzyl-P-phenethylphosphonyl)-L-alanyl-L-prolyl-L-proline L-arginine salt:

N-(O-benzyl-P-phenethylphosphonyl)-L-alanyl-L-prolyl-L-proline benzylester (0.88 g, 1.4 m mole) was dissolved in acetone (5 ml) and sodium hydroxide (0.18 g, 4.5 m mole) in water (4 ml) solution was added thereto under cooling in the ice bath, and the mixture was stirred for 2 hours. To the solution water (100 ml) was added and the mixture was washed with ethyl ether (50 ml). The solution was neutralized with 1N hydrochloric acid, and the desired product was extracted with ethyl ether (100 ml). The ethyl ether solution was dried with anhydrous sodium sulfate. The thus obtained solution was distilled under reduced pressure yielding an oily N-(O-benzyl-P-phenethylphosphonyl)-L-alanyl- L-prolyl-L-proline material (0.54 g, yield: 71.6%). The thus obtained oily material (1.0 m mole) was dissolved in ethanol (4 ml) and a solution of L-arginine (0.21 g, 1.0 m mole) in water (4 ml) was added thereto. The thus obtained solution was distilled under reduced pressure. By adding further water to it and freeze-drying the mixture, N-(O-benzyl-P-phenethylphosphonyl)-L-alanyl-L-prolyl-L-proline L-arginine salt (0.59 g, yield: 60.2% from N-(O-benzyl-P-phenethylphosphonyl)-L-alanyl-L-prolyl-L-proline benzylester) was obtained.

A fixed amount of the product (sample) was heated for 19 hours at 110° C. in 6N hydrochloric acid and the thus hydrolized material was subjected to amino acid analysis. The ratio of alanine, proline and arginine obtained was 1.00:2.08:1.05.

Example 28

N-phenethylphosphonyl-L-alanyl-L-prolyl-L-proline 2 sodium salt:

N-(O-Benzyl-P-phenethylphosphonyl)-L-alanyl-L-prolyl-L-proline benzylester (0.67 g, 1.1 m mole) was dissolved in the mixture (24 ml) of water and methanol (1:1) and sodium bicarbonate (0.16 g, 2.2 m mole) was added thereto. Hydrogen gas was passed through the solution for 3 hours under atmospheric pressure at room temperature in the presence of 5% palladium carbon as a catalyst.

The catalyst was separated by filtration and the solution was distilled leaving a residue. By dissolving the residue in water and freeze-drying it, N-phenethylphosphonyl-L-alanyl-L-prolyl-L-proline 2 sodium salt (0.54 g, quantitative yield) was obtained.

A fixed amount of the product was heated for 19 hours at 110° C. in 6N hydrochloric acid. For the thus hydrolized material, amino acids were analyzed. The ratio of alanine and proline was 1.00:2.10.

NMR spectrum [D$_2$O, internal standard: DSS] ppm: 1.25 (d, 3H), 1.50~2.45 (m, 10H), 2.60~3.00 (m, 2H), 3.30~3.90 (m, 4H), 4.00~4.56 (m, 4H), 7.30 (S, 5H).

Example 29

N-Phenethylphosphonyl-L-alanyl-N-(2-indanyl)glycyl-L-proline 2 sodium salt:

A. N-t-Butyloxycarbonyl-glycyl-L-proline benzylester

L-proline benzylester hydrochloride (20 g, 82.7 m mole) was added to chloroform (200 ml) and triethylamine (8.3 g, 82.7 m mole), N-t-butyloxycarbonyl-glycine (14.5 g, 82.7 m mole), and HOBt (11.2 g, 82.7 m mole) were added thereto under cooling. To the mixture WSC hydrochloride (15.82 g, 82.7 m mole) was added dropwise.

Further, the reaction was carried out for 2 hours on ice, and next, overnight at room temperature. The reaction solution was washed with 10% citric acid, aqueous sodium chloride, 5% sodium bicarbonate and aqueous sodium chloride in order, and dried with anhydrous sodium sulfate. The solution was distilled enough under reduced pressure leaving a sticky N-t-butyloxycarbonyl-glycyl-L-proline benzylester product (31.4 g, 83.5 m mole; yield: 100%). The product gave a single spot with R$_f$=0.66 by silica gel thin layer chromatography (developing solvent, benzene:ethyl acetate=1.1, Colour forming method: spraying of 25% hydrobromic acid and 0.1% ninhydrin and heating).

NMR spectrum [CDCl$_3$, internal standard: TMS] ppm: 1.44 (S, 9H); 1.83~2.30 (m, 4H), 3.33~3.72 (m, 2H), 3.90 (d, 2H), 4.44~4.67 (m, 1H), 5.12 (S, 2H), 5.42 (br, 1H), 7.32 (S, 5H).

B. Glycyl-L-proline benzylester hydrochloride

To N-t-butyloxycarbonyl-glycyl-L-proline benzylester (25.7 g, 68.2 m mole) 4N hydrogen chloride dioxane solution (170 ml) was added and the solid material was dissolved. The mixture was stirred for 1 hour at room temperature. The mixture was evaporated under reduced pressure to obtain a half-solid glycyl-L-proline benzylester hydrochloride (20.2 g, 64.8 m mole, yield: 95%).

The product had a hygroscopicity and gave a single spot with R$_f$=0.27 by silica gel thin layer chromatography (developing solvent, chloroform:methanol:triethylamine=40:2:1, colour forming method: spraying of 0.1% ninhydrin, and heating).

NMR spectrum [CDCl$_3$, internal standard: TMS] ppm: 1.76~2.26 (m, 4H), 3.39~3.80 (m, 2H), 3.98~4.31 (m, 2H), 4.46~4.73 (m, 1H), 5.06 (S, 2H), 7.26 (S, 5H), 8.34 (br, 3H).

C. N-(2-indanyl) glycyl-L-proline benzylester

Glycyl-L-proline benzylester hydrochloride (20.0 g, 64.1 m mole) was dissolved in dried ethanol (150 ml) and indan-2-on (4.23 g, 32.1 m mole), and Molecular Sieves (3A) (5 g) were added thereto. Sodium cyanoborohydride (2.01 g, 32.1 m mole) was gradually added to the above solution while cooling with ice, and stirring. The mixture was stirred for 1 hour under cooling with ice and then stirred for 2 hours at room temperature. A little insoluble material was separated by filtration. The ethanol was removed by distillation under reduced pressure from the reaction solution. To the residue water (150 ml) and ethyl ether (200 ml) were added and the solution was adjusted to pH 1.5 with 6N hydrochloric acid while stirring to dissolve it. The ethylether layer was removed and the remaining water layer was washed with ethyl ether (200 ml). Next, to the water layer ethyl ether (400 ml) was added and the solution was adjusted to pH 8.0 with sodium bicarbonate aqueous solution. The desired product was extracted with ethyl ether and the ethyl ether layer was separated. Further, the desired product was extracted by the addition of ethyl ether (200 ml) to the water layer and the thus extracted ethyl ether solution was separated. Such extracted ethyl ether layers were combined together, and washed with the aqueous solution saturated with sodium chloride (100 ml). The ethyl ether layer was dried with anhydrous sodium sulfate, and concentrated under reduced pressure to obtain a crystal. The crystal was washed with n-hexane, obtained on the filter paper and dried to yield a white crystal of N-(2-indanyl)glycyl-L-proline benzylester (8.02 g, 21.2 m mole, yield: 33%). Melting point: 96°-98° C.

The product gave a single spot with R$_f$=0.77 and R$_f$=0.42, respectively by silica gel thin layer chromatography (Developing solvent, n-butanol:acetic acid:water=4:2:2; and chloroform:methanol:triethylamine=40:2:1, Colour forming method: spraying of 0.1% ninhydrine, and heating).

NMR spectrum [CDCl$_3$, internal standard: TMS] ppm: 1.82~2.34 (m, 4H), 2.70~3.82 (m, 9H), 4.44~4.72 (m, 1H), 5.14 (S, 2H), 7.13 (S, 4H), 7.32 (S, 5H).

D. N-t-Butyloxycarbonyl-L-alanyl-N-(2-indanyl) glycyl-L-proline benzylester

N-(2-indanyl) glycyl-L-proline benzylester (6.0 g, 15.9 m mole), N-t-butyloxycarbonyl-L-alanine (3.0 g, 15.9 m mole) and HOBt (2.1 g, 15.9 m mole) were dissolved in chloroform (60 ml) and the mixture was stirred under cooling with ice, and WSC hydrochloride (3.03 g, 15.9 m mole) was added dropwise thereto. The reaction solution was left for 4 days in a refrigerator. Next, to the reaction solution chloroform (100 ml) was added and the mixture was washed with 10% citric acid, aqueous sodium chloride, 5% sodium bicarbonate and aqueous sodium chloride in this order, and dried with anhydrous sodium sulfate. The solution was distilled under reduced pressure leaving a syrupy residue. The syrupy residue was dissolved in ethyl ether (300 ml), and water (200 ml) was added thereto. The pH value was adjusted to 1.5 with 6N hydrochloric acid and the mixture was washed. The ethyl ether layer was separated and then dried with anhydrous sodium sulfate.

Ethyl ether was removed by distillation under reduced pressure to obtain the crystal. The crystalls were washed with n-hexane and recrystalized with ethyl acetate-isopropyl ether-n-hexan to obtain a white crystal of N-t-butyloxycarbonyl-L-alanyl-N-(2-indanyl) glycyl-L-proline benzylester (3.02 g, 5.5 m mole, yield: 35%). Melting point: 135°–136° C.

The product gave a single spot with $R_f=0.63$ by silica gel thin layer chromatography (developing solvent; benzene:ethyl acetate=1:1, Colour forming method: spraying of 25% hydrobromic acid and 0.1% ninhydrin, and heating).

Unreacted starting materials of N-(2-indanyl) glycyl-L-proline benzylester (2.95 g) was recovered from the aqueous solution of pH 1.5 produced by washing the above mentioned ethyl ether phase.

NMR spectrum [CDCl$_3$, internal standard: TMS] ppm: 1.25 (d, 3H), 1.40 (S, 9H), 1.65~2.25 (m, 4H), 2.25~3.85 (m, 7H), 3.90~5.00 (m, 4H), 5.05 (S, 2H), 5.40 (d, 1H), 7.10 (S, 4H), 7.23 (S, 5H).

E. L-Alanyl-N-(2-indanyl) glycyl-L-proline benzylester hydrochloride

N-t-butyloxycarbonyl-L-alanyl-N-(2-indanyl) glycyl-L-proline benzylester (2.72 g, 4.95 m mole) was dissolved in 4N hydrogen chloride dioxane solution (50 ml) and the mixture was stirred for 1 hour at room temperature. The solvent was distilled under reduced pressure from the solution, and thereby a sticky residue was obtained. After addition of ethyl ether the solution was filtered and a crystalline residue was obtained on the filter paper, and immediately dried in a desiccator to obtain a white powder of L-alanyl-N-(2-indanyl) glycyl-L-proline benzylester hydrochloride (2.31 g, 4.76 m mole, yield: 96%). This product had a hygrospic nature, and gave a single spot with $R_f=0.42$ by silica gel thin layer chromatography (developing solvent, chloroform:methanol:triethylamine=40:2:1, Colour forming method: spraying of 0.1% ninhydrin and heating).

NMR spectrum [CDCl$_3$, internal standard: TMS] ppm: 1.20 (2xd, 3H), 1.37~2.45 (m, 4H), 2.50~3.90 (m, 7H), 3.93~5.00 (m, 4H), 5.10 (S, 2H), 7.15 (S, 4H), 7.30 (S, 5H), 8.40 (br, 3H).

F. N-(O-benzyl-P-phenethylphosphonyl)-L-alanyl-N-(2-indanyl) glycyl-L-proline benzylester L-alanyl-N-(2-indanyl) glycyl-L-proline benzylester hydrochloride (1.5 g, 3.09 m mole) was dissolved in methylene dichloride (15 ml), and triethylamine (1.03 g, 10.2 m mole) was added thereto. Monobenzylphenethylphosphochloridate produced from dibenzylphenethylphosphonate (1.61 g, 4.4 m mole) was dissolved in methylene dichloride (10 ml). This solution was dropwise added to the above solution under cooling with ice bath and further stirred for 2 hours at room temperature. The reaction solution was washed with water, and the solvent was distilled off under reduced pressure. The residue was dissolved in ethyl acetate, and the resulting solution was washed with 1N hydrochloric acid, water, 5% sodium bicarbonate and water in this order, and dried with anhydrous sodium sulfate. The solution was distilled under reduced pressure leaving a sticky residue. The residue was purified by column chromatography (silica gel, developing solvent; ethyl acetate, methanol=20:1) to obtain N-(O-benzyl-P-phenethylphosphonyl)-L-alanyl-N-(2-indanyl) glycyl-L-proline benzylester (1.03 g, 1.46 m mole; yield: 47%).

This product gave a single spot with $R_f=0.32$, by thin layer chromatography (developing solvent, benzene:ethyl acetate=1:1, Colour forming method: spraying of 25% hydrobromic acid and 0.1% ninhydrin and heating).

NMR spectrum [CDCl$_3$, internal standard: TMS] ppm: 1.20~1.55 (m, 3H), 1.65~2.30 (m, 6H), 2.50~4.70 (m, 13H), 4.80~5.17 (m, 4H), 7.10 (S, 4H), 7.15 (S, 5H), 7.25 (S, 5H), 7.30 (S, 5H).

G. N-Phenethylphosphonyl-L-alanyl-N-(2-indanyl) glycyl-L-proline 2 sodium salt

N-(O-Benzyl-P-phenethylphosphonyl)-L-alanyl-N-(2-indanyl) glycyl-L-proline benzylester (0.74 g, 1.0 m mole) was dissolved in a mixture (30 ml) of water and ethanol (2:3) and sodium bicarbonate (0.176 g, 2.0 m mole) was added thereto. Hydrogen gas was passed through the solution for 3 hours at room temperature and atmospheric pressure in the presence of 5% palladium carbon as a catalyst. The catalyst was separated by filtration and the solution was distilled under reduced pressure until a residue was obtained. By dissolving the residue in water and freeze-drying it, N-phenethylphosphonyl-L-alanyl-N-(2-indanyl) glycyl-L-proline 2 sodium salt (0.57 g, yield: 95.4%) was obtained.

NMR spectrum [D$_2$O, internal standard: DSS] ppm: 1.05~1.52 (m, 3H), 1.55~2.35 (m, 6H), 2.40~ about 4.30 (m, 13H: peak masked partially with water), 7.28 (S, 4H), 7.35 (S, 5H).

Example 30

N-(O-Benzyl-P-phenethylphosphonyl)-L-alanyl-N-(2-indanyl) glycyl-L-proline L-arginine salt:

A. N-t-Butyloxycarbonyl-glycyl-L-proline methylester L-proline methylester hydrochloride (13.6 g, 82.7 m mole) was suspended in chloroform (200 ml) and to the suspended solution triethylamine (8.3 g, 82.7 m mole) was added while cooling. To the solution, N-t-butyloxycarbonyl glycine (14.5 g, 82.7 m mole) was added and WSC hydrochloride (15.82 g, 82.7 m mole) was gradually added thereto while cooling with ice. The reaction was carried out for 2 hours while cooling with ice, and next overnight at room temperature. The reaction solution was washed with 10% citric acid, aqueous sodium chloride, 5% sodium bicarbonate and aqueous sodium chloride in order, and dried with anhydrous sodium sulfate. The solution was distilled under reduced pressure leaving a syrupy N-t-butyloxycarbonyl-glycyl-L-proline methylester product (22.5 g, 78.5 m mole, yield: 95%). This product gave a single spot with $R_f=0.48$ by silica gel thin layer chromatography (developing solvent, benzene:ethyl acetate=1:1, colour forming method: spraying of 25% hydrobromic acid and 0.1% ninhydrin and heating).

NMR spectrum [CDCl$_3$, internal standard: TMS] ppm: 1.44 (S, 9H), 1.92~2.32 (m, 4H), 3.45~3.75 (m, 2H), 3.7 (S, 3H), 3.92 (d, 2H), 4.40~4.55 (m, 1H), 5.54 (br, 1H).

B. Glycyl-L-proline methylester hydrochloride

N-t-Butyloxycarbonyl-glycyl-L-proline methylester (21.3 g, 74.4 m mole) and 4N hydrogen chloride dioxan solution (150 ml) were mixed, and shaked to dissolve the solid material. It was stirred for 1 hour at room temperature. The solvent was well-distilled off under reduced pressure to obtain the solid glycyl-L-proline methylester hydrochloride (16.4 g, 73.9 m mole, yield: 99%). The product was very hygroscopic and gave a single spot with $R_f=0.45$ by silica gel thin layer chromatography (developing solvent, n-butanol:acetic acid:-water=4:2:2, colour forming method: spraying of 0.1% ninhydrin and heating).

NMR spectrum [CDCl$_3$, internal standard: TMS] ppm: 1.84~2.40 (m, 4H), 3.48~4.27 (m, 4H), 3.67 (S, 3H), 4.34~4.65 (m, 1H), 8.22 (br, 3H).

C. N-(2-indanyl) glycyl-L-proline methylester hydrochloride

Glycyl-L-proline methylester hydrochloride (16.0 g, 72.1 m mole) was dissolved in methanol (150 ml), and Indan-2-on (4.75 g, 36.0 m mole) and triethylamine (1.8 g, 18.0 m mole) were added thereto. Sodium syanoborohydride (2.27 g, 36.0 m mole) was gradually added thereto while cooling with ice and stirring. The mixture was stirred for 1 hour while cooling with ice and next for 5 hours at room temperature. A little insoluble material was separated by filtration, and the filtrate was concentrated under reduced pressure. To the residue, water (100 ml) and ethyl ether (100 ml) were added, and the solution was adjusted to pH 1.5 with 6N hydrochloric acid while stirring to dissolve it. The ethyl ether layer was removed, and the remaining water layer was washed with ethyl ether (100 ml). The desired product was extracted from the water layer with chloroform (100 ml×3 times). The thus obtained chloroform as extracted was concentrated under reduced pressure until a tar-like residue was obtained. To thus produced tar-like residue ethyl ether and 5% sodium bicarbonate (200 ml) were added and the mixture was stirred to dissolve the solid matter. The aqueous layer was removed and the ethyl ether layer was washed with an aqueous solution saturated with sodium chloride. To the ethyl ether layer water (150 ml) was added, and the solution was adjusted to pH 1.5 with 6N hydrochloric acid while stirring and ethyl ether was removed. The water layer was washed with ethyl ether (100 ml) and to the water layer chloroform (200 ml) was added. The solution was adjusted to pH 8.0 with sodium bicarbonate while stirring. The aqueous layer was removed, and chloroform layer was dried with anhydrous sodium sulfate, and the sodium sulfate was separated by filtration. Separately, anhydrous hydrogen chloride gas was brown into the chloroform, and thus obtained hydrogen chloride chloroform solution was added to the above mentioned chloroform layer. After checking to ascertain that the pH of the solution had been preserved, a distillation was carried out under reduced pressure, to yield N-(2indanyl) glycyl-L-proline methylester hydrochloride (4.50 g, 13.3 m mole, yield: 37%).

This product gave a single spot respectively in the $R_f=0.73$ and $R_f=0.58$, by silica gel thin layer chromatography (developing solvent, n-butanol:acetic acid:-water=4:2:2, and chloroform:methanol:triethylamine=40:2:1, colour forming method:'spraying of 0.1% ninhidrin and heating).

NMR spectrum [CDCl$_3$, internal standard: TMS] ppm: 1.81~2.38 (m, 4H), 3.26 (d, 4H), 3.40~3.93 (m, 4H), 3.66 (S, 3H), 4.03 (t, 1H), 4.40~4.66 (m, 1H), 5.29 (S, 2H), 7.16 (S, 4H)

D. N-t-Butyloxycarbonyl-L-alanyl-N-(2-indanyl) glycyl-L-proline methylester

N-(2-indanyl) glycyl-L-proline methylester hydrochloride (4.33 g, 12.8 m mole), N-t-butyloxycarbonyl-L-alanine (2.42 g, 12.8 m mole) and HOBt (1.73 g, 12.8 m mole) were dissolved in chloroform (50 ml), and triethylamine (1.29 g, 12.8 m mole) was added thereto while cooling to −15° C. and then WSC hydrochloride (2.45 g, 12.8 m mole) was gradually added thereto under cooling with ice. Further, the reaction was carried out for 2 hours on ice and next overnight at room temperature. The reaction solution was washed with 10% citric acid, aqueous sodium chloride, 5% sodium bicarbonate, and aqueous sodium chloride in order, and dried with anhydrous sodium sulfate. The solution was concentrated under reduced pressure to obtain the syrupy material (3.88 g). It was further purified by column chromatography (silica gel, developing solvent, chloroform and next ethyl acetate) to obtain N-t-butyloxycarbonyl-L-alanyl-N-(2-indanyl) glycyl-L-proline methylester (2.42 g, yield: 64%). The product gave a single spot with $R_f=0.4$ by thin layer chromatography (developing solvent, ethyl acetate:benzene=1:1, colour forming method: spraying of 25% hydrobromic acid and 0.1% ninhydrin and heating).

NMR spectrum [CDCl$_3$, internal standard: TMS] ppm: 1.30 (d, 3H), 1.45 (S, 9H), 1.75~2.40 (m, 4H), 2.70~3.85 (m, 7H), 3.70 (S, 3H), 3.90~5.10 (m, 4H), 5.45 (d, 1H), 72.0 (S, 4H).

N-(2-indanyl) glycyl-L-proline methylester hydrochloride (2.08 g) was recovered from the 10% citric acid solution which was used for washing the above mentioned reaction mixture.

E. L-Alanyl-N-(2-indanyl) glycyl-L-proline methylester hydrochloride

N-t-Butyloxycarbonyl-L-alanyl-N-(2-indanyl) glycyl-L-proline methylester (2.24 g, 4.7 m mole) was dissolved in 4.8N hydrogen chloride dioxane solution and stirred for 1 hour at room temperature. The solution was distilled off under reduced pressure leaving a residue and diethyl ether was added to the residue to obtain L-alanyl-N-(2-indanyl) glycyl-L-prolyl methylester hydrochloride crystals (1.63 g, yield: 84.1%).

NMR spectrum [D$_2$O, internal standard: DSS] ppm:1.03~1.37 (m, 3H), 1.60 (br, 3H), 1.75~2.55 (m, 4H), 2.55~3.60 (m, 7H), 3.75 (S, 3H), 3.85~ about 4.5 (m, 4H, peak partially masked with water), 7.30 (S, 4H).

F. N-(O-Benzyl-P-phenethylphosphonyl)-L-alanyl-N-(2-indanyl) glycyl-L-proline methylester L-Alanyl-N-(2-indanyl) glycyl-L-proline methylester hydrochloride (1.0 g, 2.4 m mole) was dissolved in methylene dichloride (7 ml) and triethylamine (0.77 g, 7.6 m mole) was added thereto. Monobenzylphenethyl-phosphochloridate produced from dibenzylphenethyl-phosphate (1.33 g, 3.6 m mole) was dissolved in methylene dichloride (3 ml). This solution was dropwise added to the above solution while cooling in the ice bath. The mixture was stirred overnight at room temperature. To the reaction solution methylene dichloride (50 ml) was added, and thus obtained mixture was washed with 1N hydrochloric acid, water, 5% sodium bicarbonate and water in order and dried with anhydrous sodium sulfate. The solution was distilled under reduced pressure leaving a sticky material (1.83 g). The thus obtained material was purified by column chromatography (silica gel, developing solvent, ethyl acetate, and next, ethyl acetate:methanol=20:1) to obtain N-(O-benzyl-P-phenethylphosphonyl)-L-alanyl-N-(2-idanyl) glycyl-L-proline methylester (0.65 g, yield: 42.2%). The product gave a single spot with $R_f=0.25$ by thin layer chromatography (developing solvent, ethyl acetate, colour forming method: spraying of 25% hydrobromic acid and 0.1% ninhydrin and heating).

NMR spectrum [CDCl$_3$, internal standard: TMS] ppm: 1.35 (m, 3H), 1.70~2.50 (m, 6H), 2.60~3.85 (m, 9H), 3.65 (S, 3H), 3.85~4.70 (m, 4H), 4.97 (d, 2H), 5.47 (br, 1H), 7.20 (S, 9H), 7.30 (S, 5H).

G. N-(O-Benzyl-P-phenethylphosphonyl)L-alanyl-N-(2-indanyl) glycyl-L-proline

N-(O-Benzyl-P-phenethylphosphonyl)-L-alanyl-N-(2-indanyl) glycyl-L-proline methylester (0.58 g, 0.9 m mole) was dissolved in acetone (3 ml), and a sodium hydroxide solution (0.11 g, 2.8 m mole) in water (3 ml) was added thereto, while cooling in the ice bath. The mixture was stirred for 1 hour. To this solution water (100 ml) was added and the mixture was washed with ethyl ether (50 ml). The ether-washed mixture was neutralized with 1N hydrochloric acid and the desired product was extracted with ethyl acetate. The ethyl acetate layer was dried with anhydrous sodium sulfate and the solvent was distilled off under reduced pressure to obtain a sticky N-(O-benzyl-P-phenethylphosphonyl)-L-alanyl-N-(2-indanyl) glycl-L-proline (0.53 g, yield: 93.5%).

NMR spectrum [CDCl$_3$, internal standard: TMS] ppm: 1.20~1.50 (m, 3H), 1.60~2.32 (m, 4H), 2.40~4.75 (m, 11H), 4.90 (d, 2H), 7.03 and 7.10 (2xS, 9H), 7.23 (S, 5H).

H. N-(O-Benzyl-P-phenethylphosphonyl)-L-alanyl-N-(2-indanyl) glycyl-L-proline L-arginine salt N-(O-benzyl-P-phenethylphosphonyl)-L-alanyl-N-(2-indanyl) glycyl-L-proline (0.53 g, 0.9 m mole) was dissolved in ethanol (4 ml) and the aqueous solution produced by dissolving L-arginine (0.17 g, 0.9 m mole) in water (4 ml) was added thereto. The solution was distilled under reduced pressure leaving a residue and water was added thereto. By freeze-drying a, N-(O-benzyl-P-phenethylphosphonyl)-L-alanyl-N-(2-indanyl) glycyl-L-proline L-arginine salt product (0.64 g, yield: 94.5%) was obtained. The product gave a single spot with $R_f=0.25$ for peptide in the free form and a single spot with $R_f=0$ for arginine, respectively, by thin layer chromatography (developing solvent, acetonitrile:acetic acid=30:1, Colour forming method: spraying of 25% hydrobromic acid and 0.1% ninhydrine, and heating).

Example 31

Dibenzylphosphoryl-L-alanyl-N-(2-indanyl)-glycyl-L-proline L-arginine salt:

A. Dibenzylphosphoryl-L-alanyl-N-(2-indanyl)-glycyl-L-proline methylester

L-alanyl-N-(2-indanyl) glycyl-L-proline methylester hydrochloride (1.44 g, 3.5 m mole) was dissolved in chloroform (20 ml), and triethylamine (1.1 g, 10.9 m mole) was added thereto. Dibenzylphosphorylchloride, which had been produced from dibenzyl hydrogenphosphite (0.86 g, 3.5 m mole) in the same manner as described in Example 1, was dissolved in carbon tetrachloride (10 ml). This solution was dropwise added to the above produced solution in the ice bath. The mixture was stirred overnight at room temperature. The thus precipitated triethyl amine hydrochloride was removed by filtration and the solvent was distilled off under reduced pressure. The residue was dissolved in ethyl acetate, washed with 1N hydrochloric acid, water, 5% sodium bicarbonate and water in order, and dried with anhydrous sodium sulfate. The solution was distilled under reduced pressure leaving a candy-like residue (1.64 g). This residue was purified by column chromatography (silica gel, developing solvent; ethyl acetate:methanol=80:1) to obtain dibenzylphosphoryl-L-alanyl-N-(2-indanyl)-glycyl-L-proline methylester (1.08 g, 48.5%). This product gave a single spot with $R_f=0.66$ by thin layer chromatography (Developing solvent, ethyl acetate:methanol=80:1, Colour forming method: spraying of 25% hydrobromic acid and 0.1% ninhydrine, and heating).

NMR spectrum [CDCl$_3$, internal standard: TMS] ppm: 1.10~1.50 (m, 3H), 1.65~2.25 (m, 4H), 2.55~3.82 (m, 7H), 3.65 (S, 3H), 3.85~4.80 (m, 4H), 5.00 (d, 4H), 5.45 (br, 1H), 7.16 (S, 4H), 7.35 (S, 10H).

C. Dibenzylphosphoryl-L-alanyl-N-(2-indanyl)-glycyl-L-proline Dibenzylphosphoryl-L-alanyl-N-(2-indanyl) glycyl-L-proline methylester (0.79 g, 1.2 m mole) was dissolved in acetone (5 ml), and sodium hydroxide (0.15 g, 3.8 m mole) in water (4 ml) solution was added thereto while cooling in the ice bath. The mixture was stirred for 1 hour. To this solution water (100 ml) was added, and thereafter the thus formed solution was washed with ethyl ether (50 ml). The ether washed solution was neutralized with 1N hydrochloric acid, and therefrom the desired product was extracted with ethyl acetate. The thus extracted solution was dried with anhydrous sodium sulfate, and the solvent was distilled off under reduced pressure to obtain an oily dibenzylphosphoryl-L-alanyl-N-(2-indanyl) glycyl-L-proline (0.77 g, yield: 99.7%).

NMR spectrum (CDCl$_3$, internal standard: TMS] ppm: 1.10~1.55 (m, 3H), 1.65~2.30 (m, 4H), 2.40~4.80 (m, 11H), 5.00 (d, 4H), 7.15 (S, 4H), 7.33 (S, 10H).

D. Dibenzylphosphoryl-L-alanyl-N-(2-indanyl) glycyl-L-proline L-arginine salt

Dibenzylphosphoryl-L-alanyl-N-(2-indanyl)-glycyl-L-proline (0.77 g, 1.2 m mole) was dissolved in ethanol (4 ml), and the aqueous solution produced by dissolving L-arginine (0.25 g, 1.2 m mole) in water (4 ml), was added thereto. The solvent was distilled off under reduced pressure, and then water was added thereto. This water solution was freeze-dried to obtain dibenzylphosphoryl-L-alanyl-N-(2-indanyl) glycyl-L-proline L-arginine salt (0.84 g, yield: 85.2%). This product gave a single spot having an $R_f=0.2$ for the peptide in free form, and an $R_f=0$ for arginine, respectively, by thin layer chromatography (developing solvent, acetonitrile:acetic acid=30:1, Colour forming method: spraying of 25% hydrobromic acid and 0.1% ninhydrine, and heating).

Example 32

Dibenzylphosphoryl-L-alanyl-L-prolyl-L-Proline potassium salt:

To the oily dibenzylphosphoryl-L-alanyl-L-prolyl-L-proline, (2.72 g, 5 m mole) 0.1N potassium hydroxide (50 ml) was added, and the thus produced solution was freeze-dried to obtain an amorphous powder of the dibenzylphosphoryl-L-alanyl-L-prolyl-L-proline potassium salt (2.8 g).

Elementary analysis: Found C 51.58%, H 6.41%, N 6.79%; Calculation C 51.60%, H 6.13%, N 6.69% as $C_{27}H_{33}N_3O_7P.K.2.6H_2O$.

Example 33

Dibenzylphosphoryl-L-methionyl-L-prolyl-L-proline L-arginine salt:

A. Dibenzylphosphoryl-L-methionyl-L-proline methylester L-methionyl-L-prolyl-L-proline methylester hydrochloride (2.0 g, 5.1 m mole) was dissolved in methylene chloride (20 ml), and triethyl amine (1.54 g, 15.2 m mole) was added thereto. The solution was cooled at $-30°$ C., and to the cooled solution, a carbon tetrachloride solution (10 ml) of dibenzylphosphorylchloride produced from dibenzylhydrogen phosphite (1.41 g, 5.1 m mole) was added dropwise, and the mixture was further stirred overnight at room temperature. To the reaction solution, methylene chloride (100 ml) was added, and the mixture was washed with 1N hydrochloric acid, water, 5% sodium bicarbonate and water in this order. The mixture was dried with anhydrous sodium sulfate, and the solvent was evaporated under reduced pressure to obtain a candy-like residue (3.23 g). The residue was purified by column chromatography (silica gel, developing solvent; ethyl acetate:-methanol=20:1) to obtain dibenzylphosphoryl-L-methionyl-L-prolyl-L-proline methylester (1.87 g, yield: 59.6%). A single spot with $R_f=0.1$ was obtained by thin layer chromatography (developing solvent, ethyl acetate:methanol32 20:1, Colour forming method, spraying of 25% hydrobromic acid and 0.1 ninhydrin, and heating).

NMR spectrum [CDCl$_3$, internal standard: TMS] ppm: 1.55~2.30 (m, 10H), 2.03 (S, 3H), 2.60 (t, 2H), 3.30~3.85 (m, 4H), 3.65 (S, 3H), 3.90~4.25 (br, 1H), 4.35~4.65 (m, 3H), 5.00 (2xd, 4H), 7.30 (S, 10H).

B. Dibenzylphosphoryl-L-methionyl-L-prolyl-L-proline L-arginine salt

Dibenzylphosphoryl-L-methionyl-L-prolyl-L-proline methylester (1.87 g, 3.0 m mole) was dissolved in acetone (18 ml), and 1N sodium hydroxide (4.5 ml) was added thereto under cooling and the mixture was stirred for 4 hours. To the solution, water (100 ml) was added, and the solution was washed with diethyl ether. Ethyl acetate (200 ml) was added thereto and the mixture was adjusted to pH 2 with 1N hydrochloric acid while stirring strongly. The ethyl acetate phase was separated and dried over anhydrous sodium sulfate. The solvent was evaporated to obtain an oily dibenzylphosphoryl-L-methionyl-L-prolyl-L-proline (1.81 g, yield: 99.1%). All of the thus obtained product (3.0 m mole) was dissolved in ethanol (15 ml) and a L-arginine (0.58 g, 3.0 m mole) water (5 ml) solution was added thereto. The solvent was evaporated, water was added thereto, and the thus obtained solution was freeze-dried to obtain dibenzylphosphoryl-L-methionyl-L-prolyl-L-proline L-arginine salt (2.27 g, yield: 98.7% from dibenzylphosphoryl-L-methionyl-L-prolyl-L-proline methylester). This product gave a single spot respectively having a $R_f=0.8$ for peptides in the free form and an $R_f=0.25$ for arginine by thin layer chromatography (developing solvent, n-butanol:acetic acid:water=2:1:1, Colour forming method, spraying of 25% hydrobromic acid and 0.1 ninhydrin, and heating). After hydrolysis of the product with 6N hydrochloric acid, the amino acids were analyzed. Methionine:Proline:Arginine=1.00:2.03:0.95.

Example 34

N-Phenethylphosphonyl-L-methionyl-L-prolyl-L-proline 2 sodium salt:

A. N-(O-benzyl-P-phenethylphosphonyl)-L-methionyl-L-prolyl-L-proline benzylester L-methionyl-L-prolyl-L-proline benzylester hydrochloride (5.69 g, 12.1 m mole) was dissolved in methylene chloride (30 ml), and triethylamine (3.85 g, 38.0 m mole) was added thereto. Methylene chloride solution (20 ml) of monobenzylphenethyl phosphochloridate produced from dibenzylphenethyl phosphonate (6.33 g, 17.3 m mole) was added dropwise to the above solution while cooling in the coolant of $-20°$ C. Further, it was stirred overnight at room temperature. To the reaction solution, methylene chloride (150 ml) was added, and the mixture was washed with 1N hydrochloric acid, water, 5% sodium bicarbonate and water in order, and dried with anhydrous sodium sulfate. The solution was distilled under reduced pressure to give a candy-like residue. This residue was purified by column chromatography (Silica gel, developing solvent; ethyl acetate:-methanol=10:1) to give N-(O-benzyl-P-phenethylphosphonyl)-L-methionyl-L-prolyl-L-proline benzylester (2.39 g, yield: 28.5%).

The product gave a single spot with $R_f=0.7$ by thin layer chromatography (developing solvent; ethyl acetate:methanol=10:1, Colour forming method: spraying of 25% hydrobromic acid and 0.1% ninhydrine, and heating).

NMR spectrum [CDCl$_3$, internal standard: TMS] ppm: 1.60~2.40 (m, 12H), 2.10 (S, 3H), 2.45~3.20 (m, 4H), 3.25~3.90 (m, 4H), 3.95~4.70 (m, 3H), 4.80~5.30 (m, 5H), 7.18 (S, 5H), 7.32 (S, 10H).

B. N-Phenethylphosphonyl-L-methionyl-L-prolyl-L-proline 2 sodium salt

N-(O-Benzyl-P-phenethylphosphonyl)-methionyl-L-prolyl-L-proline benzylester (1.195 g, 1.73 m mole) was dissolved in ethanol (15 ml), and sodium bicarbonate (0.290 g, 3.46 m mole) in water (5 ml) solution was added thereto. Hydrogen gas was passed through the above solution for 6 hours at room temperature and atmospheric pressure in the presence of 30% palladium barium carbonate as a catalyst. The catalyst was filtered off and from the filtrate the solvent was evaporated. The thus obtained residue was dissolved in water and freeze-dried to obtain N-phenethylphosphonyl-L-methionyl-L-prolyl-L-proline 2 sodium salt (0.80 g, yield: 83.3%). It gave a single spot with $R_f=0.5$ by thin layer chromatography (developing solvent; n-butanol:acetic acid:water=2:1:1, Colour forming method: spraying of 25% hydrobromic acid and 0.1% ninhydrine, and heating).

After hydrolysis of the product with 6N hydrochloric acid, the amino acids were analyzed. Methionine:-Proline=1.00:2.01.

NMR spectrum [D$_2$O, internal standard: DSS] ppm: 1.50~2.25 (m, 12H), 2.12 (S, 3H), 2.70 (m, 4H), 3.40~3.90 (m, 4H), 3.95~4.40 (m, 3H), 7.30 (S, 5H) FAB-MASS spectrum, m/e: 556 (M+1) 578 (M+Na).

Example 35

N-(O-Benzyl-P-phenethylphosphonyl)-L-methionyl-L-prolyl-L-proline L-arginine salt:

N-(O-Benzyl-P-phenethylphosphonyl)-L-methionyl-L-prolyl-L-proline benzylester (1.195 g, 1.73 m mole) was dissolved in acetone (10 ml), and 1N sodium hydroxide (2.6 ml) was added thereto under cooling in the ice bath. The mixture was stirred for 5.5 hours. To the solution water (100 ml) was added and the mixture was washed with diethyl ether, and then ethyl acetate (200 ml) was added thereto. The solution was adjusted to pH 2 with 1N hydrochloric acid while stirring vigorously.

Ethyl acetate layer was separated and dried over anhydrous sodium sulfate. The solvent was evaporated to give an oily N-(O-benzyl-P-phenethylphosphonyl)-L-methionyl-L-prolyl-L-proline (1.02 g, yield: 98.1%). All of thus obtained product (1.70 m mole) was dissolved in ethanol (15 ml), and L-arginine (0.33 g, 1.70 m mole) water (5 ml) solution was added thereto. The solvent was distilled off under reduced pressure, and further, water was added thereto. The water solution was freeze-dried to obtain N-(O-benzyl-P-phenethylphosphonyl)-L-methionyl-L-prolyl-L-proline L-arginine salt yielding 94.0% based on N-(O-benzyl-P-phenethylphosphonyl)-L-methionyl-L-prolyl-L-proline benzylester. The product gave single spots respectively in $R_f=0.7$ for peptides in the free form and $R_f=0.2$ for arginine, by thin layer chromatography (developing solvent; n-butanol:acetic acid:water=2:1:1, Color forming method; spraying of 25% hydrobromic acid and 0.1% ninhydrin, and heating).

After hydrolysis of the product with 6N hydrochloric acid, amino acids were analyzed.

Methionine:Proline:Arginine = 1.00:2.05:0.89

Example 36

$N^\alpha$-Phenethylphosphonyl-L-lysyl-L-prolyl-L-proline 2 sodium salt:

A.  $N^\alpha$-(O-Benzyl-P-phenethylphosphonyl)-$N^\epsilon$-benzyloxycarbonyl-L-lysyl-L-prolyl-L-proline benzylester $N^\epsilon$-benzyloxycarbonyl-L-lysyl-L-prolyl-L-proline benzylester hydrochloride (3.26 g, 5.4 m mole) was dissolved in methylene chloride (15 ml), and triethylamine (1.73 g, 17.1 m mole) was added thereto. Methylene chloride (10 ml) solution of monobenzylphenethyl phosphochloridate produced from dibenzylphenethyl phosphonate (2.84 g, 7.8 m mole) was added dropwise and the mixture was stirred overnight at room temperature. To the reaction solution methylene chloride (100 ml) was added, and the mixture was washed with 1N hydrochloric acid, water, 5% sodium bicarbonate and water in order, and dried with anhydrous sodium sulfate. The solution was distilled under reduced pressure leaving a candy-like residue. The residue was purified with column chromatography (Silica gel, developing solvent; ethyl acetate:methanol=20:1) to obtain $N^\alpha$-(O-benzyl-P-phenethylphosphonyl)-$N^\epsilon$-benzyloxycarbonyl-L-lysyl-L-prolyl-L-proline benzylester (1.21 g, yield: 27.1%). The product gave a single spot with $R_f=0.35$ by thin layer chromatography (developing solvent; ethyl acetate:methanol=20:1, Colour forming method: spraying of 25% hydrobromic acid and 0.1% ninhydrin, and heating).

B. $N^\alpha$-Phenethylphosphonyl-L-lysyl-L-prolyl-L-proline 2 sodium salt $N^\alpha$-(O-Benzyl-P-phenethylphosphonyl)-$N^\epsilon$-benzyloxycarbonyl-L-lysyl-L-prolyl-L-proline benzylester (1.21 g, 1.5 m mole) was dissolved in methanol (18 ml), and sodium bicarbonate (0.247 g, 2.9 m mole) water (5 ml) solution was added thereto. Hydrogen gas was passed through the solution for 3 hours at room temperature and atmospheric pressure in the presence of 5% palladium carbon as a catalyst. The catalyst was removed by filtration. The solvent was evaporated and the residue was dissolved in water. The solution was freeze-dried to obtain $N^\alpha$-phenethylphosphonyl-L-lysyl-L-prolyl-L-proline 2 sodium salt (0.84 g which is yielded quantitatively).

The product gave a single spot with $R_f=0.3$ by thin layer chromatography (developing solvent; n-butanol:acetic acid:water=2:1:1, Colour forming method: spraying of 25% hydrobromic acid and 0.1% ninhydrin, and heating).

After hydrolysis of the product with 6N hydrochloric acid, amino acids were analyzed. Lysine:Proline = 1.00:2.02

Example 37

$N^\alpha$-(O-Ethyl-P-phenethylphosphonyl)-L-lysyl-L-prolyl-L-proline L-arginine salt:

A. Diethylphenethylphosphonate

Diethyl phosphite (27.64 g, 200 m mole) was dissolved in DMF (200 ml), and to the solution at nitrogen atmosphere while stirring and $-15°$ C., sodium hydride (60% in oil, 9.6 g, 220 m mole) was added. The mixture was stirred for 1 hour at not more than 0° C. To the solution phenethyl bromide (37.0 g, 200 m mole) was dropwise added and further the mixture was stirred overnight at room temperature. The DMF solution was distilled under reduced pressure leaving a residue, and the residue was dissolved in ethyl acetate. The ethyl acetate solution was washed with water, and dried with anhydrous sodium sulfate. The solvent was evaporated and the thus obtained oily product was distilled under reduced pressure to obtain diethylphenethylphosphonate (25.0 g, yield: 51.6%) of boiling point $136.5° \sim 137.5°$ C./3 mmHg.

B. Monoethylphenethyl phosphochloridate

Diethylphenethyl phosphonate (1.73 g, 7.1 m mole) was dissolved in carbon tetrachloride (5 ml) and phosphorus pentachloride (1.55 g, 7.4 m mole) was added to the solution under cooling in the ice bath. The mixture was stirred for 30 minutes. The mixture was heated to 70° C. at the rate of 10° C./15 minutes, and stirred for 30 minutes at 70° C. The solution was distilled under reduced pressure in the rotary evaporator to eliminate the solvent and phosphorusoxychloride. Thus produced monoethyl phenethyl phosphochloridate was used without further purification for the following reaction.

C. $N^\alpha$-(O-Ethyl-P-phenethylphosphonyl)-$N^\epsilon$-benzyloxycarbonyl-L-lysyl-L-prolyl-L-proline benzylester $N^\epsilon$-Benzyloxycarbonyl-L-lysyl-L-prolyl-L-proline benzylester hydrochloride (3.0 g, 5.0 m mole) was dissolved in methylene chloride (15 ml), and triethylamine (1.59 g, 15.7 m mole) was added thereto. Methylene chloride (10 ml) solution of monoethylphenethyl phosphochloridate produced from diethylphenethylphosphonate (1.73 g, 7.1 m mole) was added dropwise to the above solution while cooling in the coolant at $-20°$ C. Further, the mixture was stirred overnight at room temperature. To the reaction solution methylene chloride (100 ml) was added, and the mixture was washed with 1N hydrochloric acid, water, 5% sodium bicarbonate and water in order and dried with anhydrous sodium sulfate. The solution was distilled under reduced pressure leaving a candy-like residue. The residue was purified by column chromatography (Silica gel, developing solvent; ethyl acetate:methanol=20:1) to obtain $N^\alpha$-(O-ethyl-P-phenethyl phosphonyl)-$N^\epsilon$-benzyloxycarbonyl-L-lysyl-L-prolyl-L-proline benzylester (2.92 g, yield: 76.9%). The product gave a single spot with $R_f=0.15$ by thin layer chromatography (developing solvent; ethyl acetate:methanol=20:1, Colour forming method: 25% hydrobromic acid and 0.1% ninhydrine, and heating).

D. N$^\alpha$-(O-Ethyl-P-phenethylphosphonyl)-L-lysyl-L-prolyl-L-proline L-arginine salt N$^\alpha$-(O-Ethyl-P-phenethylphosphonyl)-N$^\epsilon$-benzyloxycarbonyl-L-lysyl-L-prolyl-L-proline benzylester (1.46 g, 1.9 m mole) was dissolved in ethanol (10 ml), and L-arginine (0.40 g, 1.9 m mole) in water (5 ml) solution was added thereto. Hydrogen gas was passed through the solution for 5 hours at atmospheric pressure and room temperature in the presence of 5% palladium carbon as a catalyst. The catalyst was removed by filtration and the solvent was evaporated. The thus obtained residue was dissolved in water and freeze-dried to obtain N$^\alpha$-(O-ethyl-P-phenethylphosphonyl)-L-lysyl-L-prolyl-L-proline L-arginine salt (1.06 g, yield: 77.7%). The product gave single spots, respectively having a R$_f$=0.55 for free peptides and R$_f$=0.2 for arginine by thin layer chromatography (developing solvent; n-butanol:acetic acid:water=2:1:2, Colour forming method: spraying of 25% hydrobromic acid and 0.1% ninhydrine, and heating).

After hydrolysis of the product with 6N hydrochloric acid, amino acids were analyzed.
Lysine:Proline:Arginine=1.00:2.02:0.96

Example 38

N-n-Amylphosphonyl-L-alanyl-L-prolyl-L-proline 2 sodium salt:

A. Monobenzyl n-amylphosphochloridate

Dibenzyl n-amylphosphonate (2.74 g, 8.2 m mole) was dissolved in carbon tetrachloride (5 ml), and phosphorus pentachloride (1.80 g, 8.6 m mole) was added to the solution while cooling in the ice bath, and the mixture was stirred for 30 minutes. The mixture was heated to 70° C. at the rate of 10° C./15 minutes, and further stirred for 30 minutes at 70° C. The solution was distilled under reduced pressure in the rotary evaporator to eliminate the solvent, phosphorus oxychloride and benzylchloride. It was confirmed that the starting materials did not remain in the reaction solution by silica gel thin layer chromatography (developing solvent; benzene:ethyl acetate=1:1, Confirmation of spot: UV lamp). The thus produced monobenzyl n-amylphosphochloridate was used without further purification for the following reactions:

B. N-(O-benzyl-P-n-amylphosphonyl)-L-alanyl-L-prolyl-L-proline benzylester

L-Alanyl-L-prolyl-L-proline benzylester hydrochloride (2.37 g, 5.8 m mole) was dissolved in methylene chloride (15 ml), and triethylamine (1.84 g, 18.2 m mole) was added thereto. A methylene chloride (10 ml) solution of monobenzyl-n-amylphosphochloridate produced from dibenzyl n-amylphosphonate (2.74 g, 8.2 m mole) was dropwise added to the above solution while cooling in the coolant at −15° C. The mixture was further stirred overnight at room temperature. To the reaction solution, methylene chloride (100 ml) was added, and the mixture was washed with 1N hydrochloric acid, water, 5% sodium bicarbonate and water and dried over anhydrous sodium sulfate. The solvent was distilled off under reduced pressure to obtain a candy-like residue. It was purified by column chromatography (Silica gel, developing solvent; ethyl acetate:methanol=20:1) to obtain N-(O-benzyl-P-n-amylphosphonyl)-L-alanyl-L-prolyl-L-proline benzylester (1.26 g, yield: 36.5%). The product gave a single spot with R$_f$=0.2 by thin layer chromatography (developing solvent; ethyl acetate:methanol=20:1, Colour forming method: spraying of 25% hydrobromic acid and 0.1% ninhydrine, and heating).

NMR spectrum [CDCl$_3$, internal standard: TMS] ppm: 0.87(t,3H), 1.15~1.50(m,7H), 1.55~1.70(m,2H), 1.80~2.40(m,10H), 3.23~3.90(m,4H), 3.95~4.35(m,1H), 4.45~4.70(m,2H), 4.85~5.30(m,5H), 7.30(S,10H).

C. N-n-Amylphosphonyl-L-alanyl-L-prolyl-L-proline 2 sodium salt

N-(O-Benzyl-P-n-amylphosphonyl)-L-alanyl-L-prolyl-L-proline benzylester (1.26 g, 2.1 m mole) was dissolved in ethanol (20 ml), and sodium bicarbonate (0.354 g, 4.2 m mole) in water (20 ml) solution was added thereto. Hydrogen gas was passed through the solution at room temperature and atmospheric pressure for 3 hours in the presence of 5% palladium carbon as a catalyst. The catalyst was removed by filtration, and the solvent was evaporated. Thus obtained residue was dissolved in water and freeze-dried to obtain N-n-amylphosphonyl-L-alanyl-L-prolyl-L-proline 2 sodium salt (0.93 g, yield: 95.6%). The product gave a single spot with R$_f$=0.3 by thin layer chromatography (developing solvent; n-butanol:acetic acid:water=2:1:1, Colour forming method: spraying of 25% hydrobromic acid and 0.1% ninhydrine, and heating).

After hydrolysis of the product with 6N hydrochloric acid, amino acids were analyzed. Alanine:Proline=1.00:1.99

NMR spectrum [D$_2$O, internal standard: DSS] ppm: 0.86(t,3H), 1.02~1.70(m,9H), 1.75~2.50(m,10H), 3.35~4.35(m,7H).

Example 39

Diphenethylphosphinyl-L-alanyl-L-prolyl-L-proline sodium salt:

A. Diphenethyl phosphinic acid

Diethyl phosphite (6.9 g, 50 m mole) was added dropwise to the Grignard reagent solution produced from phenethylbromide (27.5 g, 148 m mole) and magnesium (3.6 g, 148 m mole) in anhydrous diethyl ether (100 ml) while cooling in the ice bath. The mixture was refluxed by heating overnight, and then the remaining Grignard reagent was decomposed by the addition of 1N hydrochloric acid (100 ml) and the diethyl ether was evaporated. Bromine was added to the solution while stirring in the ice bath to give a faintly brown coloured solution. The desired product was extracted with chloroform from the solution. The chloroform layer was dried with anhydrous sodium sulfate, and the chloroform was distilled off under reduced pressure. The thus obtained residue was dissolved in hot ethanol, and the solution was cooled to obtain diphenyl phosphinic acid (10.01 g, yield: 73.0%).

NMR spectrum [CDCl$_3$, internal standard: TMS] ppm: 1.80~2.23 (m, 4H), 2.70~3.10 ppm (m, 4H), 7.18 (S, 10H), 11.70 (S, 1H).

B. Diphenethylphosphinylchloride

Diphenethylphosphinic acid (1.67 g, 6.1 m mole) was dissolved in carbon tetrachloride (5 ml), and sulfuryl chloride (1.46 g, 10.8 ml) was added thereto, and the mixture was heated while refluxing for 2 hours. It was confirmed that the starting material did not remain by tracement of the NMR spectrum. The solvent and excess sulfuryl chloride were distilled off under reduced pressure to obtain an oily diphenethylphosphinylchloride, which was supplied for the following reaction.

C. Diphenethylphosphinyl-L-alanyl-L-prolyl-L-proline benzylester

L-Alanyl-L-prolyl-L-proline benzyl ester hydrochloride (2.0 g, 4.9 m mole) was dissolved in chloroform (20 ml), triethyl amine (1.36 g, 13.4 m mole) was added thereto. Chloroform (8 ml) solution of diphenethyl phosphinyl chloride produced from diphenethylphosphinic acid (1.67 g, 6.1 m mole) was added dropwise to the above solution while cooling in the coolant at −20° C. After the addition, the mixture was stirred for 1 hour at not more than 0° C., and next, overnight at room temperature. To the reaction solution chloroform (100 ml) was added, and the mixture was washed with 1N hydrochloric acid, water, 5% sodium bicarbonate and water in order, and dried over anyhydrous sodium sulfate. The solvent was distilled off under reduced pressure to obtain the residue. The residue was re-crystalized with ethyl acetate to obtain diphenethyl phosphinyl-L-alanyl-L-prolyl-L-proline benzylester (1.19 g, yield: 38.7%) of melting point 146°~147° C. The product gave a single spot with $R_f$=0.3 by thin layer chromatography (developing solvent; ethyl acetate:methanol=10:1, Colour forming method; spraying of 25% hydrobromic acid and 0.1% ninhydrine, and heating).

NMR spectrum [CDCl$_3$, internal standard: TMS] ppm: 1.40 (d, 3H), 1.75~2.35 (m, 12H), 2.65~3.05 (m, 4H), 3.20~3.90 (m, 5H), 4.20 (q, 1H), 4.50~4.75 (m, 2H), 5.10 (q, 2H), 7.20 (S, 10H), 7.32 (S, 5H).

D. Diphenethylphosphinyl-L-alanyl-L-prolyl-L-proline sodium salt

N-Diphenethylphosphinyl-L-alanyl-L-prolyl-L-proline benzylester (0.77 g, 1.2 m mole) was dissolved in methanol (20 ml), and sodium bicarbonate (0.103 g, 1.2 m mole) in water (10 ml) solution was added thereto. Hydrogen gas was passed through the above solution at room temperature and atmospheric pressure for 3 hours in the presence of 5% palladium carbon as a catalyst. The catalyst was removed by filtration, and the solvent was evaporated. The thus obtained residue was dissolved in water and freeze-dried to obtain diphenethyl phosphinyl-L-alanyl-L-prolyl-L-proline sodium salt (0.69 g, which is quantitative). The product gave a single spot with $R_f$=0.65 by thin layer chromatography (developing solvent; n-butanol:acetic acid:water=2:1:1, Colour forming method; spraying of 25% hydrobromic acid and 0.1% ninhydrine, and heating).

After hydrolysis of the product with 6N hydrochloric acid, amino acids were analyzed. Alanine:Proline=1.00:2.01.

NMR spectrum [CDCl$_3$, internal standard: TMS] ppm: 1.40(d,3H), 1.55~2.35(m,12H), 2.60~3.00(m,4H), 3.30~3.80(m,4H), 3.90~4.30(m,2H), 4.40~4.70(m,1H), 4.75~5.20(br,1H), 7.20(S,10H).

Example 40~52

| Example No. | Product | Example No., to which the same reaction was applied | Starting Materials | T.L.C. Rf value | Amino Acids Analysis, Treatment of 6N HCl |
|---|---|---|---|---|---|
| 40 | N—(O—ethyl-P—phenethylphosphonyl)-L-methionyl-L-prolyl-L-proline L-arginine salt | 39 | monoethylphenethylphosphochloridate; L-methionyl-L-prolyl-L-proline methylester hydrochloride | n-butanol:acetic acid:water = 2:1:1 Rf = 0.65 (free peptide), Rf = 0.2 (L-Arginine) | Met:Pro:Arg = 1.00:2.05:0.99 |
| 41 | N—(O—methyl-P—phenethylphosphonyl)-L-methionyl-L-prolyl-L-proline L-arginine salt | 39 | monomethylphenethylphosphochloridate; L-methionyl-L-prolyl-L-proline methylester hydrochloride | n-butanol:acetic acid: water = 2:1:1 Rf = 0.65 (free peptide), Rf = 0.2 (L-arginine) | Met:Pro:Arg = 1.00:2.01:0.97 |
| 42 | N—(O—benzyl-P—phenethylphosphonyl)-L-alanyl-L-prolyl-L-proline sodium salt | 26 and 27 | monobenzylphenethylphosphochloridate; L-alanyl-L-prolyl-L-proline methylester hydrochloride | n-butanol:acetic acid: water = 2:1:1 Rf = 0.8 | Ala:Pro = 1.00:2.01 |
| 43 | N—(O—ethyl-P—phenethylphosphonyl)-L-alanyl-L-prolyl-L-proline sodium salt | 39 | monoethylphenethylphosphochloridate; L-alanyl-L-prolyl-L-proline benzylester hydrochloride | n-butanol:acetic acid: water = 2:1:1 Rf = 0.75 | Ala:Pro = 1.00:2.04 |
| 44 | Diethylphosphoryl-L-methionyl-L-prolyl-L-proline L-argine salt | 23 | Diethylphosphorylchloride; L-methionyl-L-prolyl-L-proline methylester hydrochloride | n-butanol:acetic acid: water = 2:1:1 Rf = 7.0(free peptide) Rf = 0.2(L-arginine) | Met:Pro:Arg = 1.00:2.02:0.98 |
| 45 | N—(O—ethyl-P—phenethylphosphonyl)-L-alanyl-L-prolyl-L-proline ethylester | 39 | monoethylphenethylphosphochloridate; L-alanyl-L-prolyl-L-proline ethylester hydrochloride | ethyl acetate: methanol = 20:1 Rf = 0.1 | Met:Pro = 1.00:2.05 |
| 46 | N—phenethylphosphonyl-L-alanyl-L-prolyl-L-proline ethylester sodium salt | 43 | monobenzylphenethylphosphochloridite; L-alanyl-L-prolyl-L-proline ethyl ester hydrochloride | n-butanol:acetic: water = 2:1:1 Rf = 0.5 | Ala:Pro = 1.00:1.99 |
| 47 | N—phenethylphosphonyl-L-alanyl-L-prolyl-L-proline 2 arginine salt | 26 and 28 | monobenzylphenethylphosphochloridate; L-alanyl-L-prolyl-L-proline benzylester hydrochloride | n-butanol:acetic acid: water = 2:1:1 Rf = 0.4(free peptide) Rf = 0.2(L-arginine) | Ala:Pro:Arg = 1.00:2.01:1.98 |
| 48 | N—(3-phenylpropyl)phosphonyl-L-alanyl-L-prolyl-L-proline 2 sodium salt | 26 and 28 | monobenzyl(3-phenylprophyl)-phosphochoridate; L-alanyl-L-prolyl-L-proline benzylester hydrochloride | n-butanol:acetic acid: water = 2:1:1 Rf = 0.35 | Ala:Pro = 1.00:2.02 |
| 49 | N—benzylphosphonyl-L-alanyl-L-prolyl-L-proline 2 sodium salt | 26 and 28 | monobenzylbenzylphosphochloridate; L-alanyl-L-prolyl-L-proline benzylester hydrochloride | n-butanol:acetic acid: water = 2:1:1 Rf = 0.6 | Ala:Pro = 1.00:2.05 |

-continued

| Example No. | Product | Example No., to which the same reaction was applied | Starting Materials | T.L.C. Rf value | Amino Acids Analysis, Treatment of 6N HCl |
|---|---|---|---|---|---|
| 50 | N—(O—ethyl-P—phenethylphosphonyl)-L-lysyl-L-prolyl-L-proline ethylester hydrochloride | 39 | monoethylphenethylphosphochloridate; N$^\epsilon$—benzyloxycarbonyl-L-lysyl-L-prolyl-L-proline ethylester hydrochloride | n-butanol:acetic acid:water = 2:1:1 Rf = 0.3 | Lys:Pro = 1.00:2.05 |
| 51 | N—(O—ethyl-P—phenethylphosphonyl)-L-lysyl-L-prolyl-L-proline | 39 | monoethylphenethylphosphocholoridate; N$^\epsilon$—benzyloxycarbonyl-L-lysyl-L-prolyl-L-proline benzylester hydrochloride | n-butanol:acetic acid:water = 2:1:1 Rf = 0.55 | Lys:Pro = 1.00:2.01 |

Example 52

N-Phenethylphosphonyl-L-alanyl-L-prolyl-L-proline methylester sodium salt:

A. N-(O-Benzyl-P-phenethylphosphonyl)-L-alanyl-L-prolyl-L-proline methylester L-Alanyl-L-prolyl-L-proline methylester hydrochloride (3.3 g, 10.0 mmole) was dissolved in methylene chloride (30 ml), and thiethylamine (3.03 g, 30.0 mmole) was added thereto.

Methylene chloride (20 ml) solution of monobenzylphenethylphosphochloridate produced from dibenzylphenethylphosphonate (5.23 g, 14.3 mmole) was added dropwise to the above solution while cooling in the ice bath. The mixture was stirred overnight at room temperature. To the reaction solution methylene chloride (150 ml) was added, and the mixture was washed with 1N hydrochloric acid, water, 5% sodium bicarbonate and water in order, and dried with anhydrous sodium sulfate. The solvent was distilled off under reduced pressure to obtain a candy-like residue. It was purified by column chromatography (Silica gel, developing solvent; ethyl acetate:methanol=10:1) to give N-(O-benzyl-P-phenethylphosphonyl)-L-alanyl-L-prolyl-L-proline methylester (1.91 g, yield: 34.4%). The product gave a single spot with Rf=0.2 by thin layer chromatography (developing solvent; ethylacetate:methanol=2:1, Colour forming method: spraying of 25% hydrobromic acid and 0.1% ninhydrine, and heating).

NMR spectrum [CDCl$_3$, internal standard: TMS] ppm: 1.33(2 x d, 3H), 1.75~2.40(m,10H), 2.60~3.15(m,2H), 3.25~3.90(m,4H), 3.68(S,3H), 4.00~4.35(br,1H), 4.50~4.75(m,3H), 4.98(2 x d, 2H), 7.20(S,5H), 7.35(S,5H).

B. N-Phenethylphosphonyl-L-alanyl-L-prolyl-L-proline methylester sodium salt

N-(O-Benzyl-P-phenethylphosphonyl)-L-alanyl-L-prolyl-L-proline methylester (1.21 g, 2.2 mmole) was dissolved in ethanol (20 ml), and sodium bicarbonate (0.18 g, 2.2 mmole) in water (5 ml) solution was added thereto. Hydrogen gas was passed through the above solution for 90 minutes at room temperature and atmospheric pressure in the presence of 5% palladium carbon as a catalyst. The catalyst was removed by filtration, and the solvent was distilled off. The thus obtained residue was dissolved in water, and the solution was freeze-dried to obtain N-phenethyl-phosphonyl-L-alanyl-L-prolyl-L-proline methylester sodium salt (0.95 g, yield: 89.5%). The product gave a single spot with Rf=0.45 by thin layer chromatography (developing solvent; n-butanol:acetic acid:water=2:1:1, Colour forming method: spraying of 25% hydrobromic acid and 0.1% ninhydrine, and heating). NMR spectrum [CDCl$_3$, internal standard: TMS] ppm: 1.20(d,3H), 1.50~2.35(m,10H), 2.55~3.05(m,2H), 3.20~4.10 (m,5H), 3.65(S,3H), 4.25~4.90(m,3H), 7.10(s,5H).

Example 53

An antihypertensive activity of part of the amino acid derivatives prepared above was determined.

As subject animals there were used 2 SHR which had been trained enough and been confirmed to be hypertensive spontaneously hypertenisive rats (male, 13 months of age, the body weight of 400~440 g) per sample.

As an instrument for measuring the blood pressure there was used Programmed Electro-Sphygmomanometer PE-300 (Narco Co., U.S.A.), and the blood pressure was indirectly measured on conscious rats.

An aqueous solution or suspension of a sample (35 mg/kg) was once force-fed into the stomach by means of a peroral probe.

Table 1 shows the results.

TABLE 1

| Sample | Systolic Blood Pressure, mmHg | | |
|---|---|---|---|
| | Pretreatment | 4 hrs after administration | ΔBlood Pressure |
| Example | | | |
| 1 | 205 | 170 | −35 |
| 2 | 202 | 180 | −22 |
| 3 | 208 | 197 | −11 |
| 4 | 207 | 195 | −12 |
| 5 | 188 | 173 | −15 |
| 6 | 212 | 190 | −22 |
| 8 | 196 | 177 | −19 |
| 12 | 193 | 182 | −11 |
| 13 | 181 | 162 | −19 |
| 14 | 183 | 161 | −22 |
| 15 | 182 | 167 | −15 |
| 16 | 181 | 162 | −19 |
| 17 | 182 | 163 | −19 |
| 18 | 192 | 171 | −21 |
| 19 | 196 | 181 | −15 |
| 20 | 184 | 169 | −15 |
| 21 | 191 | 167 | −24 |
| 22 | 206 | 196 | −10 |
| 23 | 190 | 165 | −25 |
| 24 | 192 | 161 | −31 |
| 25 | 183 | 156 | −27 |
| 26 | 182 | 160 | −22 |
| 27 | 180 | 152 | −28 |
| 28 | 183 | 151 | −32 |
| 29 | 203 | 172 | −31 |
| 30 | 184 | 154 | −30 |
| 31 | 199 | 169 | −30 |
| 32 | 185 | 160 | −25 |
| 33 | 186 | 168 | −18 |
| 34 | 183 | 154 | −29 |
| 35 | 191 | 158 | −33 |

TABLE 1-continued

| | Systolic Blood Pressure, mmHg | | |
|---|---|---|---|
| Sample | Pretreatment | 4 hrs after administration | ΔBlood Pressure |
| 36 | 200 | 177 | −23 |
| 37 | 201 | 172 | −29 |
| 38 | 187 | 167 | −20 |
| 39 | 195 | 172 | −23 |
| 40 | 196 | 166 | −30 |
| 41 | 203 | 172 | −31 |
| 42 | 194 | 180 | −14 |
| 43 | 195 | 171 | −24 |
| 44 | 189 | 179 | −10 |
| 52 | 193 | 183 | −10 |
| * | 198 | 193 | −5 |

*Dibenzyl phosphoryl-L-alanyl-L-proline L-arginine salt

Example 54

Dry packed capsules containing 50 mg/capsule of an active ingredient were prepared.

| | |
|---|---|
| Dibenzylphosphoryl-L-alanyl-L-prolyl-L-proline L-arginate | 50 mg |
| Lactose | 149 mg |
| Magnesium stearate | 1 mg |
| Capsule (size No. 1) | 200 mg |

An amino acid derivative was reduced to a No. 60 powder. Lactose and magnesium stearate were passed through a No. 60 sieve cloth to fall over the foregoing powder and mixed sufficiently with it. The mixture was packed into No. 1 dry gelatin capsules.

Example 55

There were prepared tablets containing dibenzylphosphoryl-L-alanyl-L-prolyl-L-proline L-arginate (25 mg), pregelatinized starch (82 mg), microcrystalline cellulose (82 mg), and magnesium stearate (1mg). In place of the foregoing amino acid derivative, other amino acid derivatives described hereinbefore could be made into tablets together with pregelatinized starch, microcrystalline cellulose, and magnesium stearate.

Tablets for combined use containing a diuretic such as hydrochlorothiazide were prepared by incorporating therein dibenzylphosphoryl-L-alanyl-L-prolyl-L-proline-L-arginate (7.5 mg), hydrochlorothiazide (50 mg), pregelatinized starch (82 mg), microcrystalline cellulose (82 mg), and magnesium stearate (1 mg).

The foregoing results demonstrate that the amino acid derivatives of the present invention are useful as an antihypertensive drug or an intermediate for preparation thereof.

Having now fully described the invention, it will be apparent to one of ordinary skill in the art that many changes and modificaitons can be made thereto without departing from the spirit or scope of the invention as set forth therein.

What is claimed as new and desired to be secured by Letters Patent of the United States is:

1. An amino acid derivative represented by the formula:

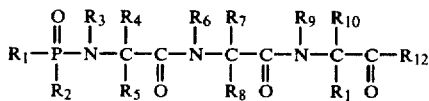

wherein:
$R_1$ and $R_2$ are the same or different from each other, and each individually represents hydroxy, alkyloxy, aryloxy, aralkyloxy, alkyl, aryl, or aralkyl;

$R_3$, $R_5$, $R_8$, and $R_{11}$, at least two of which are the same or all of which are different from one another, and each individually represents a hydrogen atom or lower alkyl;

$R_4$, $R_7$, and $R_{10}$, at least two of which are the same, or all of which are different from one another, and each individually represents a hydrogen atom, or lower alkyl, lower allyl, benzyl or indanyl, which may be further substituted by HO, CO, carbamoyl, guanidino, imidazolyl, indolyl mercapto or alkylthio;

$R_6$ and $R_9$ are the same or different from each other, and each individually represents hydrogen atom, lower alkyl, lower allyl, indanyl or benzyl; and;

$R_{12}$ represents hydroxyl, alkyloxy, aryloxy, aralkyloxy, amino, mono- or dialkyl-, aryl- or aralkylamino; and $R_6$ and $R_7$ combined together, and $R_9$ and $R_{10}$ combined together, may independently form an alkylene bridge having 2 to 4 carbon atoms which may further contain a double bond or be further substituted with hydroxyl.

2. The derivative as described in claim 1, wherein at least one of amino acids constituting said amino acid derivative is in the L-form.

3. The derivative as described in claim 1, wherein said amino acid derivative is in the salt form.

4. The derivative as described in claim 1, wherein $R_3$, $R_5$, $R_8$ and $R_{11}$ are hydrogen atoms.

5. The derivative described in claim 1, wherein:
$R_1$ and $R_2$ are the same or different from each other, and each individually represents hydroxyl, a lower alkyloxy having 1 to 5 carbon atoms, an aryloxy having 6 to 12 carbon atoms, an aralkyloxy having 6 to 12 carbon atoms, a lower alkyl having 1 to 5 carbons atoms, an aryl having 6 to 12 carbon atoms, or an aralkyl having 6 to 12 carbon atoms;

$R_3$, $R_5$, $R_8$, and $R_{11}$, at least two of which are the same, or all of which are different from one another, and each individually represents hydrogen atom or a lower alkyl having 1 to 5 carbon atoms;

$R_4$, $R_7$, and $R_{10}$, at least two of which are the same, or all of which are different from one another, and each individually represents a hydrogen atom, or lower alkyl having 1 to 5 carbon atoms, lower allyl having 1 to 5 carbon atoms, indanyl or benzyl, which may be further substituted by HO, CO, carbomoyl, guanidino, imidazolyl, indolyl, mercapto or alkylthio, $R_6$ and $R_9$ are the same or different from each other, and each individually represents a hydrogen atom, a lower alkyl having 1 to 5 carbon atoms, an allyl having 6 to 12 carbon atoms, indanyl or benzyl; and $R_{12}$ represents hydroxyl, a lower alkyl having 1 to 5 carbon atoms, an aryloxy having 6 to 12 carbon atoms, aralkyloxy having 6 to 12 carbon atoms, an amino, mono- or di-lower alkyl amino having 1 to 5 carbon atoms, aryl amino having 6 to 12 carbon atoms, or alkyl amino having 6 to 12 carbon atoms.

6. The derivative described in claim 1, wherein when an alkyl, an aryl or an aralkyl represented at $R_4$, $R_7$ and $R_{10}$ has at least one substituent, the substituent is an organic group selected from the group consisting of hydroxyl, carboxyl, carbamoyl, amino, guanidino, imidazolyl, indolyl, mercapto and lower alkylthio.

7. The derivative described in claim 1, wherein $R_6$ and $R_7$ combined together, or $R_9$ and $R_{10}$ claimed together, form an alkylene bridge having at least one substituent, the substituent is an organic group selected from the group consisting of hydroxyl, lower alkoxy, lower alkyl, oxo, condensed aryl ring and a condensed alicyclic ring.

8. The derivative described in claim 1, wherein:

$R_1$ and $R_2$ are the same or different from each other, and individually represent an organic group selected from the group consisting of hydroxyl, methoxy, ethoxy, n-propyloxy, n-butyloxy, phenoxy, benzyloxy, phenethyloxy, methyl, ethyl, n-propyl, n-butyl, n-pentyl, phenyl, benzyl, phenethyl, and phenylpropyl;

$R_3$, $R_5$, $R_8$ and $R_{11}$ represent a hydrogen atom, or at least one of them represents methyl instead of the hydrogen atom;

$R_4$, $R_7$ and $R_{10}$, at least two of which are the same, or all of which are different from one another, each individually represents an organic group selected from the group consisting of hydrogen atom, methyl, isobutyl, phenyl, benzyl, hydroxybenzyl, hydroxymethyl, carboxymethyl, carboxyethyl, carbamoylmethyl, carbamoylethyl, aminopropyl, aminobutyl, aminopentyl, guanidinopropyl, imidazolylmethyl, indolylmethyl, mercaptomethyl and methylthioethyl;

$R_6$ and $R_9$ are the same or different from each other, and each individually represents an organic group selected from the group consisting of hydrogen atom, methyl, cyclopropyl, cyclopentyl, cyclohexyl, 2-indanyl and 1-indanyl; and $R_{12}$ represents an organic group selected from the group consisting of hydroxyl, methyloxy, ethyloxy, benzyloxy, amino, methylamino, ethylamino and phenyloxy.

9. The derivative as described in claim 1, wherein when $R_6$ and $R_7$ are combined together, or $R_9$ and $R_{10}$ are combined together, the structure of the combination is anyone of the following:

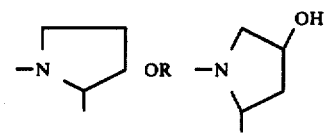

10. The derivative as described in claim 3, wherein said salt is one selected from the group consisting of sodium salt, potassium salt, lithium salt, ammonium salt, dicyclohexylamine salt, t-butylamine salt and basic amino acid salt.

11. An antihypertensive drug which comprises 0.2–2,000 mg of at least one of the amino acid derivatives represented by the formula:

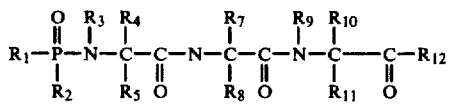

wherein $R_1$ and $R_2$ are the same or different from each other, and each individually represents hydroxyl, alkyloxy, aryloxy, aralkyloxy, alkyl, aryl, or aralkyl;

$R_3$, $R_5$, $R_8$, and $R_{11}$, at least two of which are the same, or all of which are different from one another, and each individually represents hydrogen atom or lower alkyl;

$R_4$, $R_7$, and $R_{10}$, at least two of which are the same, or all of which are different from one another, and each individually represents a hydrogen atom, or lower alkyl, lower allyl, benzyl or indanyl, which may be further substituted by HO, CO carbamoyl, guanidino, imidazolyl, indolyl, mercapto or alkylthio;

$R_6$ and $R_9$ are the same or different from each other, and each individually represents a hydrogen atom, lower alkyl, lower allyl, benzyl or indanyl; and $R_{12}$ represents hydroxyl, alkyloxy, aryloxy, aralkyloxy, amino, mono- or di-alkyl-, aryl-, or aralkylamino; and $R_6$ and $R_7$ combined together, and $R_9$ and $R_{10}$ combined together, may independently form an alkylene bridge having 2 to 4 carbon atoms, which may further contain a double bond or be further substituted with hydroxyl and a pharmceutically acceptable carrier.

12. The antihypertensive drug described in claim 11, wherein at least one of amino acids constituting said amino acid derivative is in the L-form.

13. The antihypertensive drug described in claim 11, wherein said amino acid derivative is in the form of a pharmaceutically acceptable salt.

14. The antihypertensive drug described in claim 11, which further comprises a diuretic.

* * * * *

UNITED STATES PATENT AND TRADEMARK OFFICE
CERTIFICATE OF CORRECTION

PATENT NO. : 4,472,381

DATED : September 18, 1984

INVENTOR(S) : Sakakibara et al.

It is certified that error appears in the above-identified patent and that said Letters Patent is hereby corrected as shown below:

Under the heading "Assignees" change "Ajinomoto Company Incorporated" to --Ajinomoto Co., Inc.--.

Under the heading "ABSTRACT", in the formula, change

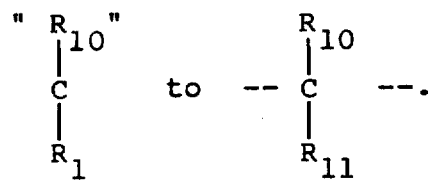

Also under the heading "ABSTRACT", in the 2nd line following the formula, change "arylkyloxy" to --aralkyloxy--.

| Col. | Line | |
|---|---|---|
| 1 | 17 | In the formula, change |

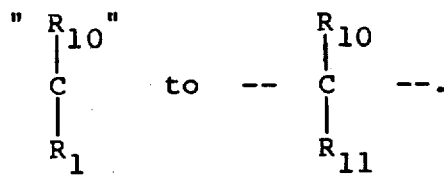

UNITED STATES PATENT AND TRADEMARK OFFICE
CERTIFICATE OF CORRECTION

PATENT NO. : 4,472,381

DATED : September 18, 1984

INVENTOR(S) : Sakakibara et al.

It is certified that error appears in the above-identified patent and that said Letters Patent is hereby corrected as shown below:

| Col. | Line | |
|---|---|---|
| 2 | 5 | Change "amino guanidino" to --amino, guanidino--; also line 5, change "indolyl mer-" to --indolyl, mer- --. |
| 6 | 48 | Change "$\frac{7}{8}$" to -- $\frac{1}{3}$ --. |
| 8 | 7 | Change "hyddrogen" to --hydrogen--. |
| 11 | 15 | Change "P-toluene" to --p-toluene--. |
| 12 | 28 | Delete "ma-". |
| 12 | 29 | Delete "terial" (first occurrence). |
| 12 | 52 | Change "nyl L" to --nine L--. |
| 12 | 63 | Delete "the". |
| 12 | 65 | Delete "material". |
| 13 | 21 | Delete "hydro-". |
| 13 | 22 | Delete "chloric". |
| 13 | 29 | Delete "material". |
| 13 | 67 | Delete "material". |

UNITED STATES PATENT AND TRADEMARK OFFICE
CERTIFICATE OF CORRECTION

PATENT NO. : 4,472,381

Page 3 of 7

DATED : September 18, 1984

INVENTOR(S) : Sakakibara et al.

It is certified that error appears in the above-identified patent and that said Letters Patent is hereby corrected as shown below:

| Col. | Line | |
|---|---|---|
| 14 | 14 | Delete "material". |
| 16 | 60 | Delete "material". |
| 18 | 46 | Change "t-butyloxycarbonyl" to --t-Butyloxycarbonyl--. |
| 19 | 3 | Change "t-butyloxycarbonyl" to --t-Butyloxycarbonyl--. |
| 19 | 65 | Change "t-Butyloxycarbonyl" to --t-butyloxycarbonyl--. |
| 21 | 8 | Change "Prolyl" to --prolyl--. |
| 22 | 56 | Change "$\varepsilon$-carbobenzoxy" to --$N^{\varepsilon}$-benzyloxycarbonyl--. |
| 22 | 58 | Change "$\varepsilon$-carbobenzoxy" to --$N^{\varepsilon}$-benzyloxycarbonyl--. |
| 22 | 64 | Change "$\varepsilon$-carboben-" to --$N^{\varepsilon}$-benzyloxy- --. |

UNITED STATES PATENT AND TRADEMARK OFFICE
CERTIFICATE OF CORRECTION

PATENT NO. : 4,472,381            Page 4 of 7
DATED : September 18, 1984
INVENTOR(S) : Sakakibara et al.

It is certified that error appears in the above-identified patent and that said Letters Patent is hereby corrected as shown below:

| Col. | Line | |
|---|---|---|
| 22 | 65 | Change "zoxy-" to --carbonyl- --. |
| 23 | 8 | Change "ε-carbobenzoxy" to --$N^\varepsilon$-benzyloxycarbonyl--. |
| 23 | 21 | Change "ε-" to --$N^\varepsilon$- --. |
| 23 | 22 | Change "carbobenzoxy-" to --benzyloxycarbonyl- --. |
| 23 | 34 | Change "ε-carbobenzoxy" to --$N^\varepsilon$-benzyloxycarbonyl--. |
| 23 | 39 | Change "ε-carbobenzoxy" to --$N^\varepsilon$-benzyloxycarbonyl--. |
| 23 | 55 | Change "ε-carbobenzoxy" to --$N^\varepsilon$-benzyloxycarbonyl--. |
| 23 | 62 | Delete "residue". |
| 30 | 11 | Change "(2-indanyl) glycyl-" to --(2-indanyl)-glycyl- --. |

UNITED STATES PATENT AND TRADEMARK OFFICE
CERTIFICATE OF CORRECTION

PATENT NO. : 4,472,381                                    Page 5 of 7
DATED      : September 18, 1984
INVENTOR(S): Sakakibara et al.

It is certified that error appears in the above-identified patent and that said Letters Patent is hereby corrected as shown below:

| Col. | Line | |
|---|---|---|
| 31 | 25 | Change "syanobo-" to --cyanobo- --. |
| 31 | 61 | Change "(2indanyl)" to --(2-indanyl)--. |
| 34 | 22 | Delete "Dibenzylphosphoryl-L-alanyl-N-(2-inda-". |
| 34 | 23 | Before "nyl)" insert --Dibenzylphosphoryl-L-alanyl-N-(2-inda--. |
| 34 | 36 | Change "(2-indanyl) glycyl" to --(2-indanyl)-glycyl--. |
| 34 | 41 | Change "(2-indanyl) gly-" to --(2-indanyl)-gly- --. |
| 35 | 9 | Delete "L-methionyl-L-prolyl-L-proline". |
| 35 | 10 | Before "methylester" insert --L-methionyl-L-prolyl-L-proline--. |

UNITED STATES PATENT AND TRADEMARK OFFICE
CERTIFICATE OF CORRECTION

PATENT NO. : 4,472,381  
DATED : September 18, 1984  
INVENTOR(S) : Sakakibara et al.

Page 6 of 7

It is certified that error appears in the above-identified patent and that said Letters Patent is hereby corrected as shown below:

| Col. | Line | |
|---|---|---|
| 42 | | In the table, at the row of "Example No. 48", in the column under "Starting Materials", first line of that entry, change "(3-phenylprophyl)-" to --(3-phenylpropyl)- --. |
| 43 | 24 | Change "thie-" to --trie- --. |
| 45 | 63 | In the formula, change "$\overset{R_{10}}{\underset{R_{1}}{\mid\mid\mid C}}$" to --$\overset{R_{10}}{\underset{R_{11}}{\mid\mid\mid C}}$--. |
| 46 | 13 | Change "CO," to --$CO_2H$,--. |
| 46 | 14 | Before "guanidino" insert --amino, --; also line 14, change "indolyl mercapto" to --indolyl, mercapto--. |
| 46 | 52 | Change "CO," to --$CO_2H$,--. |
| 46 | 53 | Before "guanidino" insert --amino, --. |

UNITED STATES PATENT AND TRADEMARK OFFICE
CERTIFICATE OF CORRECTION

PATENT NO. : 4,472,381

DATED : September 18, 1984

INVENTOR(S) : Sakakibara et al.

It is certified that error appears in the above-identified patent and that said Letters Patent is hereby corrected as shown below:

| Col. | Line | |
|---|---|---|
| 46 | 57 | Change "allyl" to --aryl--. |
| 48 | 10 | Before "ammonium" insert --calcium salt, --. |
| 48 | 17 | In the formula, change |

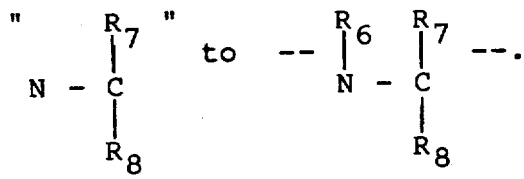

| 48 | 34 | Change "CO carbamoyl," to --$CO_2H$, carbamoyl, amino, --. |

Signed and Sealed this

Second Day of July 1985

[SEAL]

Attest:

DONALD J. QUIGG

*Attesting Officer*     *Acting Commissioner of Patents and Trademarks*